(12) United States Patent
Baier et al.

(10) Patent No.: US 12,164,686 B2
(45) Date of Patent: Dec. 10, 2024

(54) CONTROL-POINT ACTIVATION CONDITION DETECTION FOR GENERATING CORRESPONDING CONTROL SIGNALS

(71) Applicant: Iron Will Innovations Canada Inc., Lloydminster (CA)

(72) Inventors: Brent Michael Baier, Lloydminster (CA); Jesse Katzman-Beimuts, Victoria (CA); Slade Luchynski, Lloydminster (CA)

(73) Assignee: Iron Will Innovations Canada Inc., Lloydminster (CA)

( * ) Notice: Subject to any disclaimer, the term of this patent is extended or adjusted under 35 U.S.C. 154(b) by 0 days.

(21) Appl. No.: 18/311,043

(22) Filed: May 2, 2023

(65) Prior Publication Data
US 2023/0273680 A1  Aug. 31, 2023

Related U.S. Application Data

(62) Division of application No. 17/021,419, filed on Sep. 15, 2020, now Pat. No. 11,681,369.
(Continued)

(51) Int. Cl.
*G06F 3/01* (2006.01)
*A61B 5/00* (2006.01)
(Continued)

(52) U.S. Cl.
CPC ............ *G06F 3/014* (2013.01); *A61B 5/6806* (2013.01); *G06F 3/017* (2013.01); *G06F 3/0304* (2013.01); *G06F 1/163* (2013.01)

(58) Field of Classification Search
CPC ........ G06F 3/014; G06F 3/017; G06F 3/0304; G06F 1/163; G06F 3/011; G06F 3/0346; A61B 5/6806; A61B 5/27; A61B 5/1125
See application file for complete search history.

(56) References Cited

U.S. PATENT DOCUMENTS

| 4,414,537 | A | 11/1983 | Grimes |
| 5,906,004 | A | 5/1999 | Lebby et al. |

(Continued)

FOREIGN PATENT DOCUMENTS

| WO | 97/37340 A1 | 10/1997 |
| WO | 2015/048584 A1 | 4/2015 |

OTHER PUBLICATIONS

Post, et al., "Smart Fabric, or Washable Computing", http://web.media.mit.edu/~rehmi/fabric, 4 pages, Nov. 5, 2009.
(Continued)

*Primary Examiner* — William Lu
(74) *Attorney, Agent, or Firm* — THE MARBURY LAW GROUP, PLLC

(57) ABSTRACT

A device and method for detecting control-point activation conditions corresponding to a portion of a glove body coming in contact with or being within a threshold distance from at least one of another portion of the glove body or a control surface separate from the glove body. The glove may include a conductive path attached to the glove body and an expanded conductive area conductively coupled to the conductive path and attached to the glove body. The expanded conductive area may be wider than individual portions of the conductive path.

9 Claims, 16 Drawing Sheets

Related U.S. Application Data

(60) Provisional application No. 62/900,808, filed on Sep. 16, 2019.

(51) Int. Cl.
   *G06F 1/16* (2006.01)
   *G06F 3/03* (2006.01)

(56) References Cited

U.S. PATENT DOCUMENTS

| | | | |
|---|---|---|---|
| 6,080,690 A | 6/2000 | Lebby et al. | |
| 6,128,004 A | 10/2000 | McDowall et al. | |
| 6,141,643 A | 10/2000 | Harmon | |
| 6,210,771 B1 | 4/2001 | Post et al. | |
| 6,670,894 B2 | 12/2003 | Mehrin et al. | |
| 6,727,197 B1 | 4/2004 | Wilson et al. | |
| 6,729,025 B2 | 5/2004 | Farrell et al. | |
| 6,942,496 B2 | 9/2005 | Sweetland et al. | |
| 7,498,956 B2 | 3/2009 | Baier et al. | |
| 8,704,758 B1 | 4/2014 | Figlety et al. | |
| 9,501,143 B2* | 11/2016 | Pellaton | G08C 17/02 |
| 9,606,630 B2 | 3/2017 | Underkoffler et al. | |
| 10,561,367 B2 | 2/2020 | Salada et al. | |
| 10,593,101 B1 | 3/2020 | Han et al. | |
| 10,642,364 B2 | 5/2020 | Minnen | |
| 10,802,657 B1 | 10/2020 | Ahne et al. | |
| 10,852,826 B1* | 12/2020 | Cox | G06F 3/016 |
| 11,292,236 B1 | 4/2022 | Wang et al. | |
| 2002/0080031 A1* | 6/2002 | Mann | G07C 9/28 340/572.1 |
| 2004/0036678 A1 | 2/2004 | Zngf | |
| 2004/0051694 A1 | 3/2004 | Backman et al. | |
| 2004/0210166 A1 | 10/2004 | Soh et al. | |
| 2004/0263358 A1 | 12/2004 | Madsen et al. | |
| 2005/0052291 A1 | 3/2005 | Backman et al. | |
| 2005/0052412 A1 | 3/2005 | McRae et al. | |
| 2006/0248478 A1 | 11/2006 | Liau | |
| 2007/0291016 A1 | 12/2007 | Philipp | |
| 2010/0090966 A1 | 4/2010 | Gregorio | |
| 2011/0018803 A1* | 1/2011 | Underkoffler | G06F 3/017 345/158 |
| 2013/0104285 A1 | 5/2013 | Nolan | |
| 2013/0113704 A1* | 5/2013 | Sarrafzadeh | G06F 3/033 345/158 |
| 2014/0240214 A1* | 8/2014 | Liu | G06F 3/014 345/156 |
| 2015/0013044 A1 | 1/2015 | Baacke | |
| 2015/0091858 A1 | 4/2015 | Rosenberg et al. | |
| 2015/0091859 A1 | 4/2015 | Rosenberg et al. | |
| 2015/0119726 A1* | 4/2015 | Matsuno | G16H 40/67 600/483 |
| 2015/0258431 A1 | 9/2015 | Stafford et al. | |
| 2015/0357948 A1* | 12/2015 | Goldstein | G05D 7/0676 318/16 |
| 2016/0134299 A1* | 5/2016 | Lowe | G01D 5/16 341/15 |
| 2016/0165037 A1* | 6/2016 | Youn | H04W 8/005 455/557 |
| 2016/0171907 A1 | 6/2016 | Moore et al. | |
| 2016/0175186 A1* | 6/2016 | Shadduck | A61H 19/34 601/15 |
| 2016/0180594 A1 | 6/2016 | Todeschini | |
| 2016/0239091 A1* | 8/2016 | Forutanpour | G06F 1/1641 |
| 2016/0259408 A1 | 9/2016 | Messingher et al. | |
| 2016/0266606 A1* | 9/2016 | Ricci | G06F 1/163 |
| 2016/0306431 A1 | 10/2016 | Stafford et al. | |
| 2016/0342207 A1* | 11/2016 | Beran | G06F 3/011 |
| 2017/0041812 A1* | 2/2017 | Iuzzolino | H04W 24/02 |
| 2017/0086712 A1 | 3/2017 | Mauro et al. | |
| 2017/0139556 A1* | 5/2017 | Josephson | H04L 12/2803 |
| 2017/0196513 A1 | 7/2017 | Longinotti-Buitoni et al. | |
| 2017/0251440 A1* | 8/2017 | Gilson | H04W 52/028 |
| 2017/0308166 A1* | 10/2017 | Mallinson | G02B 27/017 |
| 2017/0319950 A1 | 11/2017 | Buchanan, IV et al. | |
| 2019/0101981 A1 | 4/2019 | Elias et al. | |
| 2019/0121338 A1* | 4/2019 | Cella | H04B 17/23 |
| 2019/0346938 A1 | 11/2019 | Wang et al. | |
| 2019/0361917 A1* | 11/2019 | Tran | H04W 12/108 |
| 2020/0022433 A1 | 1/2020 | Lu et al. | |
| 2020/0160748 A1* | 5/2020 | Hans | G09B 21/008 |
| 2020/0257384 A1 | 8/2020 | Ahne et al. | |
| 2022/0018689 A1 | 1/2022 | Whitehead et al. | |
| 2022/0350414 A1* | 11/2022 | Lee | G06F 3/012 |
| 2023/0185381 A1* | 6/2023 | Cho | G06N 3/047 345/156 |

OTHER PUBLICATIONS

The International Bureau of WIPO, International Preliminary Report on Patentability issued in corresponding International Application No. PCT/IB2020/000744 mailed Mar. 31, 2022, 10 pages.

Canadian Intellectual Property Office, International Search Report and the Written Opinion of the International Searching Authority issued in corresponding International Application No. PCT/IB2020/000744 dated Jan. 18, 2021, 14 pages.

* cited by examiner

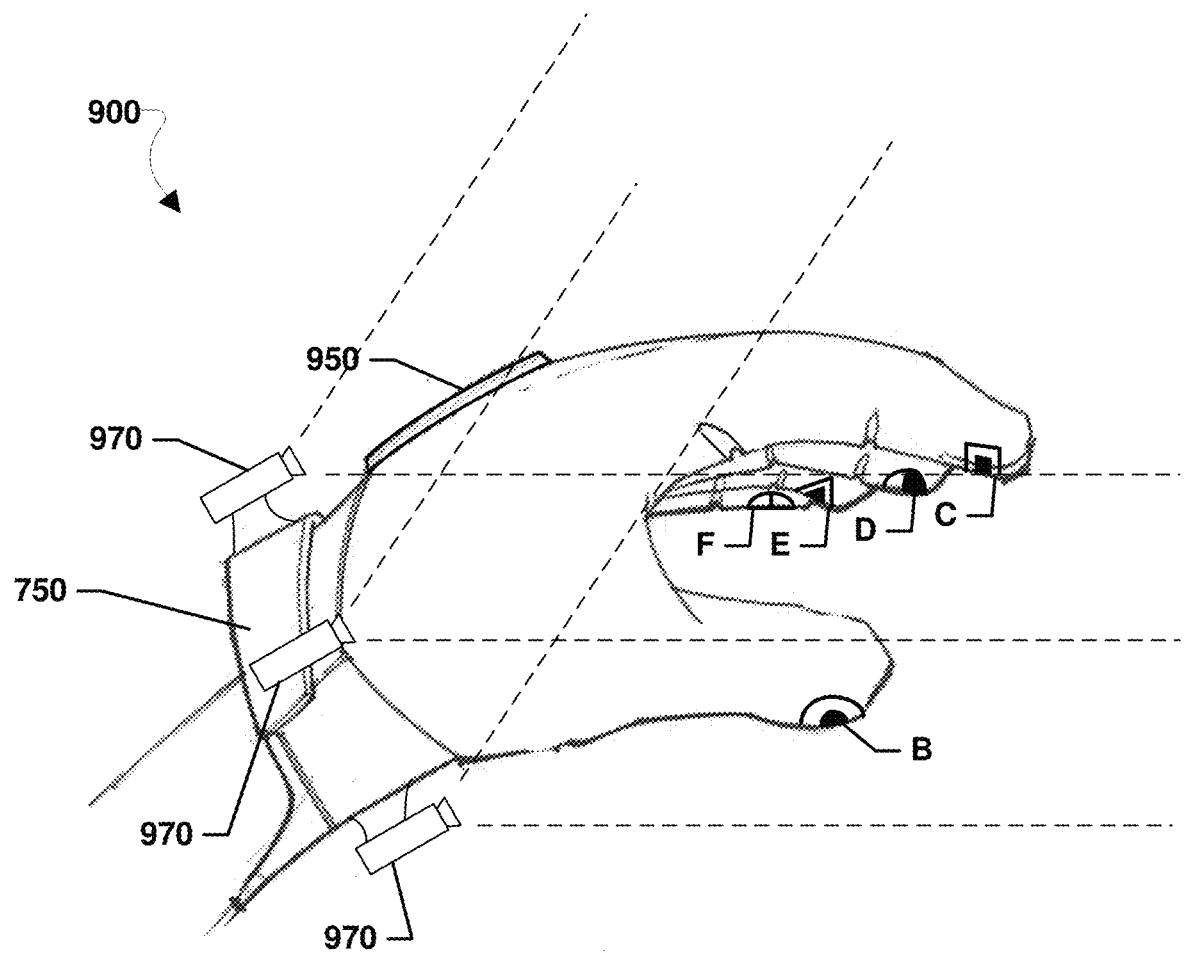
FIG. 9A
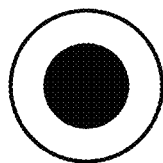 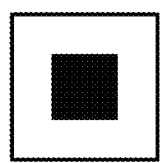 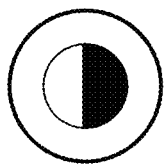 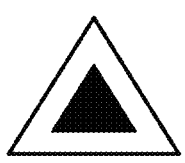 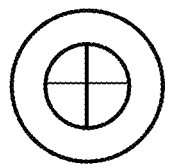
FIG. 9B    FIG. 9C    FIG. 9D    FIG. 9E    FIG. 9F

CONTROL-POINT ACTIVATION CONDITION DETECTION FOR GENERATING CORRESPONDING CONTROL SIGNALS

RELATED APPLICATIONS

This application is a Divisional Application of U.S. patent application Ser. No. 17/021,419 entitled "Control-Point Activation Condition Detection For Generating Corresponding Control Signals" filed Sep. 15, 2020 which claims the benefit of priority to U.S. Provisional Patent Application No. 62/900,808 entitled "Control-Point Activation Condition Detection For Generating Corresponding Control Signals" filed Sep. 16, 2019, the entire contents of both of which are hereby incorporated by reference for all purposes.

BACKGROUND

There are many human interface input devices for data, control, and command entry into computing devices and other systems that are in common use. These input devices are typified by a keyboard, mouse, touch pad, joystick, graphics tablet, electronic pen, and various motion sensitive or motion activated controllers. These input devices are routinely encountered in home, office, or industrial settings or in the rapidly expanding areas of console, computer, and on-line gaming. There are also many interface devices that have been custom designed for automation and robotic control or to provide alternative control and command capture methods for a wide range of specialized devices and applications.

One type of human interface input device that frees the wearer from many of the drawbacks of traditional input devices uses touch sensors directly embedded or otherwise integrated into garments, such as gloves, that are worn by an individual. Signals generated by touching these sensors are routed through various circuits sewn, woven, or otherwise integrated into or attached to the garment and conveyed to signal processing circuits mounted at strategic locations therein or that may be transmitted to signal processing circuits external to the garment. The signal processing circuits analyze these signals and construct appropriate messages corresponding to the signals that can be sent to a computer or other similar equipment to simulate or mimic traditional wearer input devices.

One common application that uses garments, such as gloves, as a human interface input device is virtual reality (VR). In VR applications, the garment wearer's movements need to be translated into virtual movements within a virtual world. There are a number of companies recreating physical instrument panels in training situations using VR with a corresponding real-world control panel training setup that the user can touch and feel. In addition to the use of VR for video gaming systems, VR has many other applications. For example, drug companies use VR to train employees when handling, mixing, or even just picking up special items. As another example, aerospace training simulators use VR to mimic a real-world cockpit or control panels therein. Similarly, VR may be used to train operators of tractors, heavy equipment, military vehicles, security stations, cranes, etc.

SUMMARY

Various embodiments include methods, systems and gloves for detecting control-point activation conditions initiated by a wearer of a glove for virtual reality applications. The glove may include a glove body that may be configured to receive a hand of the wearer therein. The glove body may include at least one finger cavity for receiving a finger of the hand, wherein the at least one finger cavity extends away from a palm region toward a fingertip region of the glove body. The glove may also include a conductive path attached to the glove body and extending from a proximal end of the at least one finger cavity, closest to the palm region, toward a distal end of the at least one finger cavity, closest to the fingertip region. In addition, the glove may include an expanded conductive area conductively coupled to the conductive path and attached to the glove body. The expanded conductive area may be wider than individual portions of the conductive path. Further, the glove may include a processor coupled to the conductive path, wherein the processor is configured to process received inputs from the expanded conductive area via the conductive path representing a control-point activation condition. The control-point activation condition may correspond to a portion of the glove body coming in contact with or being within a threshold distance from at least one of another portion of the glove body or a control surface separate from the glove body.

In various embodiments, the conductive path comprises at least one of a coiled wire and/or a conductive printed ink. In addition, a conductive thread may attach the conductive path to the glove body. The conductive area may include at least one of a capacitive sensor or an inductive sensor. A conductive thread may attach the conductive area to the conductive path. The glove body may be formed from a unitary thin elastic polymer material.

In various embodiments, the glove may include a radio frequency identification (RFID) reader may be coupled to the conductive path, wherein the RFID reader is configured to detect an RFID tag on a control surface separate from the glove body. The glove may also include a transceiver coupled to the processor and configured to transmit a message corresponding to the received input. In addition, the glove may include at least one camera mounted on the glove body and configured to obtain images of at least one finger portion of the glove body, wherein the processor is configured to process the obtained images received from the at least one camera. One or more portions of the glove body may include an imprinted code configured to be detected by the at least one camera. The glove may include at least one camera mounted on the glove body and configured to obtain images of control surface remote from the glove. A processor of the glove may be configured to process the obtained images received from the at least one camera.

Various embodiments may include methods performed by a processor (e.g., a processor within a glove or in a computing device coupled to the glove) for control-point activation detection for generating control signals. The method may include receiving a control-point input suitable for tracking location, angle, and/or relative position of one or more portions of a glove. The method may determine whether a control-point activation condition is detected and generate control signals associated with the detected control-point activation condition in response to determining the control-point activation condition is detected.

In some embodiments, the control-point input may be received from an expanded conductive area via a conductive path coupled thereto, which is attached to a glove body, wherein the expanded conductive area is wider than individual portions of the conductive path. The control-point input may be received from a camera mounted on a glove body. The control-point input may include an image of a marking visible on at least one of the glove body or a control panel surface remote from the glove. The control-point input may be received from contact between a portion of a glove and a control panel surface remote from the glove. The control-point activation condition may be received in response to a portion of a glove hovering close to at least one of another portion of the glove or a control panel surface remote from the glove.

In some embodiments, the method may include determining whether at least one of a location, an angle, or a relative position of the one or more portions of the glove has changed. In addition, a virtual image of the glove may be generated based on the changed at least one of the location, the angle, or the relative position of the one or more portions of the glove in response to determining at least one of the location, the angle, or the relative position of the one or more portions of the glove has changed. The method may further include adjusting the received control-point input with calibration parameters. The calibration parameters may be determined using at least two control-point inputs previously received for simultaneously tracking and comparing the same location, angle, or relative position of the same one or more portions of the glove.

In some embodiments, the method may include receiving an image of a glove with an object or markings of predetermined size positioned in a glove size designated location on the glove. A glove size may be determined by comparing a first imaged size of the object or markings in the image to a second imaged size of the glove in the image, using the predetermined size and designated location of the object or markings. Also, the glove size may be output based on the comparison of first and second imaged sizes.

Various embodiments may include methods performed by a processor (e.g., a processor within a glove or in a computing device coupled to the glove) for sizing a virtual reality hand. The method may include receiving an image of a glove with an object or markings of predetermined size positioned in a designated location on the glove. In addition, a glove size may be determined by comparing a first imaged size of the object or markings in the image to a second imaged size of the glove in the image, using the predetermined size and designated location of the object or markings. Also, the glove size may be output based on the comparison of first and second imaged sizes.

Various embodiments may include methods performed by a processor (e.g., a processor within a glove or in a computing device coupled to the glove) for sizing a virtual reality hand that includes receiving an image of a hand or glove and determining a virtual reality hand size or orientation by comparing the received image of the hand or glove to a previously saved image of the hand or glove. In addition, the virtual reality hand size or orientation may be output based on the comparison of the received image and the previously saved image. The received image may include indications of a visible object or markings of predetermined size positioned in a designated location on the glove. Determining the virtual reality hand size or orientation may include comparing a first imaged size and orientation of the object or markings in the received image to the previously saved image of the glove.

Various embodiments may include methods performed by a processor (e.g., a processor within a glove or in a computing device coupled to the glove) for control-point activation detection for generating control signals that includes receiving control-point input information indicating a location or region on the glove in which a first control-point activation condition occurred. Historical control-point information may be updated with the received control-point input. An order of priority may be determined for cycling through a check of locations or regions on the glove to determine whether a second control-point activation condition occurred based on the updated historical control-point information. The locations or regions on the glove may be checked, in the determined order of priority, to determine whether the second control-point activation condition occurred.

Further aspects include a glove including a processor configured with processor-executable instructions to perform operations of any of the methods summarized above. Further aspects include a non-transitory processor-readable storage medium having stored thereon processor-executable software instructions configured to cause a processor of a glove to perform operations of any of the methods summarized above. Further aspects include a processing device for use in a glove and configured to perform operations of any of the methods summarized above. Further embodiments include a computing device configured to be coupled to a glove of various embodiments and having a processor configured with processor-executable instructions to perform operations of any of the methods summarized above.

DESCRIPTION OF THE FIGURES

The accompanying drawings, which are incorporated herein and constitute part of this specification, illustrate exemplary embodiments of the invention, and together with the general description given above and the detailed description given below, serve to explain the features of the invention.

FIG. 9A is a side view of a glove with wrist-mounted cameras and surface markers according to various embodiments.

FIGS. 9B-9F are relief views of various glove markers shown on the glove in FIG. 9A according to various embodiments.

DETAILED DESCRIPTION

Figure 1:
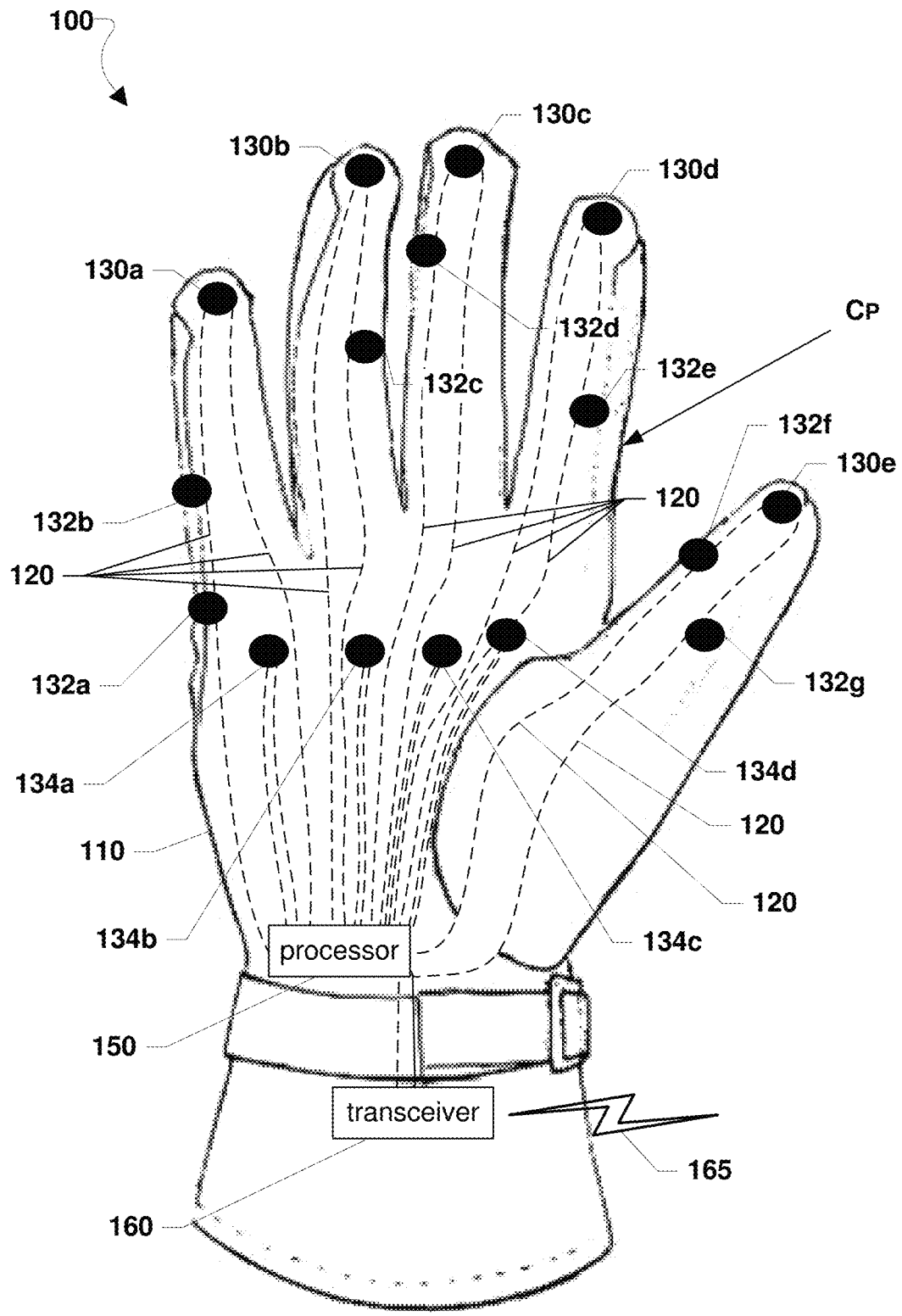
FIG. 1 is a plan view of a glove according to various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments include a glove that may be used as a human interface or input device, enabling the identification of various hand movements, gestures, finger position inputs, and/or contact with or proximity to switches or control surfaces by a wearer of a glove. Various embodiments include a glove configured to be worn by a wearer and detect a position, orientation, and/or proximity of one or more portions of the glove relative either to other portions of the glove or to particular surfaces apart from the glove. Unlike conventional input devices that map signals to an individual symbol or command, key or combination of keys, various embodiments include elements and/or techniques for identifying portions of the glove, referred to as control-points, that have come in contact with or in close proximity to either another control-point of the glove or a control surface separate from the glove.

Various embodiments include a conductive path extending across one or more portions of the glove. The conductive path may be configured to convey received inputs from control-point activation conditions, which correspond to when one or more portions of the glove come in contact with or in close proximity to either another portion of the glove or a control surface separate from the glove. A processor may analyze the received inputs conveyed along the conductive path, and/or transmit those inputs, as a message corresponding to the received inputs, to a remote processor wirelessly.

In various embodiments, the glove may include expanded conductive areas at predetermined locations along the conductive path. The expanded conductive areas may be configured to expand the detection of control-point activation conditions beyond the narrow width of the conductive path and responsive to certain finger touches. For example, expanded conductive areas may be located within a palm of the glove, at finger tips, and/or at a thumb tip. The expanded conductive areas may be configured to complete a circuit that indicates that control-point activation conditions have been met. As a more specific example, when an expanded conductive area of the glove comes in contact with or comes within close proximity of a control surface, resistance through that path is reduced and current through that path is increased indicating whether a switch associated with that control surface has been engaged or approached. Similarly, when one expanded conductive area, for example on a side or tip of a finger, comes in contact with or close proximity to another expanded conductive area, for example on a thumb, the change in resistance or capacitance through the resulting conductive path indicates a particular gesture or command has been made by a wearer of the glove. Thus, by providing the expanded conductive areas of the glove, the wearer is able to input commands, symbols or letters that correspond to certain finger touches together or to the palm.

In some embodiments, the detected change in resistance or capacitance may be conveyed to a processor located within the glove. The processor may process the signal(s) to generate an indication of whether an associated control-point activation condition has been met (e.g., a fist gesture or switch activation has occurred). The processor may alternatively or additionally pass along the generated indication, via further portions of the conductive path, to a transceiver located within the glove. The transceiver may be configured to transmit the generated indication of the associated control-point activation condition, as a message corresponding to the associated control-point activation condition.

Traditional control panel training applications that use VR have difficulty presenting accurate hand presence to the trainee. The precise position of the trainee's hand or hands in the VR space must match a real-world position of the hand or hands relative to the physical control panel on which they are training. Various embodiments are particularly suited to improve VR-based control panel training applications. For example, in accordance with various embodiment the control panel itself may be equipped with switches (i.e., control surfaces) that include metallic elements or surfaces. Thus, a glove in accordance with various embodiments, touching one of those control surfaces may act like a multimeter and measure resistance. Accordingly, a measurement of resistance by the glove may provide an indication of proximity to or contact with (also referred to herein as a "control-point activation condition") a control surface. Different icons, buttons or portions of the control surface may be configured with different resistance values, and thus the processor may determine the icon, button or panel location that was touched by the resistance through the circuit through the glove to the touched surface.

A further aspect of various embodiments includes configuring or measuring the resistance at different locations on control surfaces (e.g., buttons, switches, icons, etc.) so that each has a known resistance that can be used by the processor to recognize when a particular item is touched. The glove and processor system may be configured to detect differences in resistance of as little as 5-10 ohms. In addition, adding a resistor to a switch may change its resistance, so each control surface may be modified (i.e., by adding one or more resistors) to exhibit a unique or at least different resistance. In this way, proximity and/or activation of a particular control surface (e.g., buttons, switches, icons, etc.) may be recognized based on comparing measured resistance to the known resistance of different items on the control surface. For example, a 50-ohm reading may correspond to the control surface (i.e., switch) designated for putting an aircraft's flaps up, while a 100-ohm reading may correspond to the control surface designated for deploying landing gear.

A further aspect of various embodiments may use a grid of RFID tags embedded in or mounted on the surface of a control panel with control surfaces. Alternatively, one RFID tag may be located on each control surface, providing a unique identifier for each control surface. The RFID tags may then be read by an RFID reader included in/on or associated with the glove. The RFID reader antenna may be located in or on a suitable portion of the glove, such as embedding an antenna loop in the pointer finger or thumb portion of the glove. Alternatively, or additionally, the expanded conductive areas and conductive paths may act like an antenna between the RFID reader and the RFID tags. In addition, RFID signals may trigger on proximity and do not require contact between surfaces.

A further aspect of various embodiments relates to detecting bending of one or more fingers the glove to provide inputs useful for VR systems. In addition, the tracking and/or detection of finger movements may be used to detect certain gestures being made by a user wearing the glove. Thus, various embodiments include a glove with one or more cameras mounted on the glove and configured to obtain images of at least one finger portion of the glove body, in order to detect finger movements and bending. In addition, portions of the glove, such as the finger tips, may include a marking, such as imprinted codes, bar codes, quick response (QR) codes, or other unique symbols, which may be readily identifiable by the one or more cameras. In addition, one or more control surfaces remote from the glove may include imprinted codes, such as bar codes, quick response (QR) codes, or other unique symbols, which may be used to identify or confirm the identity of the control surface (i.e., to identify or confirm proximity or engagement with a particular switch, button, or other control).

A further aspect of various embodiments relates to scaling a wearer's hands when generating a representation of those hands in a VR environment (i.e., virtual hands). Current systems tend to take a one size fits all approach. Various embodiments perform dynamic virtual hand scaling in order to present wearers of the gloves with a more realistic representation of their actual hand size.

A further aspect of various embodiments relates to orienting a wearer's hands when generating virtual hands in a VR environment. Current systems tend to make orientation determinations based on an offset from other known system elements, like a paddle controller that may be held by the wearer. Unfortunately, this may lead to an inaccurate representation of virtual hand orientations. Various embodiments perform dynamic virtual hand orienting in order to present wearers of the gloves with a more accurate representation of the orientation of their hands.

A further aspect of various embodiments relates to improving the processing of signals received from the expanded conductive areas through the conductive paths of the glove. In order to determine whether there has been a change in resistance or capacitance at any particular location or through any particular conductive path on the glove, processors may cycle through every location on the glove, checking for a change in resistance, capacitance or other electric characteristic. Various embodiments perform smart location cycling, which takes into account the most frequent touch locations and/or most recently active locations on the glove, in order to speed up the identification of where control-point activation conditions may be occurring.

A further aspect of various embodiments may include sensors connected to one or more of the expanded conductive areas and/or one or more of the conductive paths. In this way, sensors placed in special locations on a glove may be used to detect or confirm certain hand gestures or hand movements have been made.

As used herein, the expressions a "control-point input" refers to one or more signals received from an input element of a glove. The signals may be received when certain conditions occur at a location on particular portion of a glove. For example, a conductive element at a first location on the glove may make contact with a conductive element at a second location on the glove, which forms a closed-circuit loop and generates an identifiable input associated with the two locations and is considered a control-point input. Similarly, a sensor at a particular location on the glove may trigger under certain circumstances and the triggering of that sensor, which is an identifiable input associated with a particular location on the glove is considered a control-point input. Also, camera images of a particular location on the glove in combination with image analysis may be configured to identify certain conditions associated with that location and may be considered a control-point input.

As used herein, the expression "control-point activation condition" refers to a predefined condition that occurs when one or more recognized control-point inputs are received that correspond to predetermined gestures, motions, or control surface interaction. The control surface interactions may include both direct contact or close-contact (i.e., hovering) between the glove and another portion of the glove or a control panel surface remote from the glove.

As used herein, the terms "component," "system," and the like include a computer-related entity, such as, but not limited to, hardware, firmware, a combination of hardware and software, software, or software in execution, which are configured to perform particular operations or functions. For example, a component may be, but is not limited to, a process running on a processor, a processor, an object, an executable, a thread of execution, a program, and/or a computer. By way of illustration, both an application running on a communication device and the communication device may be referred to as a component. One or more components may reside within a process and/or thread of execution and a component may be localized on one processor or core and/or distributed between two or more processors or cores. In addition, these components may execute from various non-transitory computer readable media having various instructions and/or data structures stored thereon. Components may communicate by way of local and/or remote processes, function or procedure calls, electronic signals, data packets, memory read/writes, and other known computer, processor, and/or process related communication methodologies.

As used herein, the term "proximal" refers to elements situated nearer to the center of a body, such as the body of a wearer, or nearer to the point of attachment of a portion of the body. In contrast, as used herein, the term "distal" refer to elements situated away from the center of the body or from the point of attachment; meaning the opposite of proximal.

Various embodiments provide solutions for tracking hand movement in VR applications. In particular, various embodiments may determine when a user touches a switch or control surface and which switch or control surface they are touching, approaching, or hovering over. Various aspects of the glove and related methods disclosed herein may eliminate the need to use mock instrument panels that are wired and functional to train with a VR application.

FIG. 1 illustrates a glove 100 to be worn by a wearer that may be used as an input device to a computing system in accordance with various embodiments. The glove 100 may include a glove body 110, a conductive path 120, and a processor 150, coupled to the conductive path 120, which may be configured to process received inputs from the conductive path. In particular, the conductive path 120 may convey one or more inputs (i.e., control-point inputs) that may represent control-point activation conditions or other signals received from control points. In various embodiments, control-point activation conditions may correspond to when a conductive portion of the glove 100 comes in contact with another conductive portion of the glove 100 or a conductive control surface remote from the glove 100. Additionally, the processor 150 may be configured to learn from previous touch-type control-point activation conditions for detecting non-contact control-point activation conditions, such as when a portion of the glove is hovering over another portion of the glove 100 or a control surface separate from the glove 100.

The glove body 110 may be a covering for all or part of a hand of the wearer and thus configured to receive the hand or parts of the hand therein. The glove body 110 is formed from the main sections of material configured to cover parts of the hand. Thus, the glove body 110 may include at least one finger cavity for receiving a finger of the hand. In various embodiments, the glove body 110 may include more than one finger cavity, such as a cavity for one or more other fingers or a separate cavity for each finger. As with a conventional glove, the at least one finger cavity may extend away from a palm region toward a fingertip region of the glove body 110. The glove body may be formed from any of a variety of materials and may be a combination of materials. For example, the glove body 110 may comprise a fabric blend of polyester and spandex.

The conductive path 120 may be attached to the glove body 110 and extend across the wrist, palm, and/or finger regions of the glove body 110. The conductive path 120 may extend between the processor 150 and a portion of the glove body 110 configured to receive inputs. For example, the conductive path 120 may extend from the processor 150 located at a proximal end of the glove body 110, such as the wrist region, to a fingertip region located at a distal end of at least one of the finger cavities. The conductive path 120 may form a closed-circuit loop for each extent between the proximal and distal ends. In various embodiments, the conductive path 120 may be formed from a flexible conductive material configured to bend and/or move, along with corresponding portions of the glove body 110 following hand movements of the wearer. For example, the flexible conductive material may be formed from wire, a conductive trace, conductive ink, or other conductive element. For example, the conductive path 120 may be formed as a linear resistor, such as from a forty ohm (40Ω) coiled wire, which may be soldered or otherwise bonded to a circuit board. The spiral pattern of a coiled wire, which may be 1 millimeter in width, may provide more flexibility and a wider coverage than a straight piece of wire.

In various embodiments, the glove body 110 may additionally include one or more expanded conductive areas 130a, 130b, 130c, 130d, 130e (i.e., 130a-130e), 132a, 132b, 132c, 132d, 132e, 132f, 132g (i.e., 132a-132g), 134a, 134b, 134c, 134d (i.e., 134a-134d), strategically located on the glove body in locations such as the finger tips, sides of fingers, palm, and the like. The expanded conductive areas 130a-130e, 132a-132g, and 134a-134d may provide localized surface regions in which distinct resistive changes may be detected when one or more portions of the glove 200 are touching switches, special surfaces, or other conductive areas. In this way, when thumb tip and fingertip are touching, a resistance may lower by approximately 30 ohms, indicating a switch is being touched. In addition, if the wearer slides a glove-finger along one of the expanded conductive areas 130a-130e, 132a-132g, and 134a-134d, maintaining engagement therewith, the continuous signal with changing resistance may represent control-point activation conditions associated with a slider or potentiometer operations, such as for scrolling, zooming in/out, or other functions.

In contrast to the conductive path 120, individual segments of which may be relatively narrow, the conductive areas may be formed to cover broader areas, significantly wider than the conductive path 120. Expanding the sensing capability of the conductive path, the conductive areas may connect directly or indirectly to the conductive path 120. In various embodiments, each of the expanded conductive area may be formed by a pad, patch or plate made of conductive material. For example, a first set of conductive pads may be the expanded conductive areas 130a-130e, located at or near a tip of each finger portion of the glove body 110, including the thumb. A second set of conductive pads may be the finger-side conductive pads 132a-132g, located at more central and base regions of the finger portions of the glove body 110. A third set of conductive pads may be the palm conductive pads 134a-134d, located at or near the palm portions of the glove body 110. The number and precise position of the individual conductive pads or sets of conductive pads (e.g., 130a-130e, 132a-132g, and 134a-134d) is illustrated for ease of explanation. However, more or fewer of these conductive pads may be located at any portion of the glove body 110. For example, additional conductive pads may be included on the back-side of the glove, in the orientation shown in FIG. 1. The various conductive pads may be located in predetermined locations, such that contact between or close proximity of two or more of the conductive pads may generate a signal containing a control-point input indicative of a control-point activation condition. In accordance with various embodiments, the conductive pads may include tactile features, capacitive detection, force-sensing resistor, potentiometer, proximity detection, radio frequency identification (RFID), motion sensors, thermal sensors, and/or other forms of contact and/or proximity sensors. One or more of such additional elements incorporated into or onto the conductive pads may provide additional/redundant information that may be used to confirm position, orientation, and/or sizing determinations.

Additionally, the conductive pads may be enhanced for providing proximity detection, in addition to contact detection. All or a portion of the conductive pads may be replaced with or supplemented by RFID tags embedded or attached in the fabric of the glove 100. RFID reader antennas may be located in various areas of the glove 100, such as the thumb or palm thereof. For example, the RFID reader(s) may be incorporated into the conductive pads (e.g., 130a-130e, 132a-132g, and 134a-134d). In addition, or alternatively, the RFID reader antenna may be incorporated into the conductive pads and/or the conductive path(s) (e.g., 120). By adjusting the signal strength of the RFID reader antenna, the proximity at which the RFID tags are activated may be adjusted. Thus, by using an RFID tag and reader system various proximity detections can be made. For example, the proximity may be finely tuned so that the RFID tag needs to be touched by the antenna to activate, or the proximity may be tuned so that the RFID tag only needs to come within an inch (1") of the RFID reader antenna. Alternatively, other distances or proximity methods could be used, such as measuring time between ultrasonic pulses originating from a location on the glove with receivers on the finger tips.

In some embodiments, the glove 100 may include a processor 150 which is configured to receive a generated signal and process the generated signal to identify movements, gestures, or even proximity to switches or control surfaces by a wearer with the glove 100. Although the processor 150 is shown in FIG. 1 as being located near the wrist on the palm-side of the glove 100, it should be understood that the processor and/or a related control module, housing the processor and other components or circuitry, may be located elsewhere on the glove. For example, the processor 150 and the related control module may be located on the back of the glove (e.g., see control module 850 in FIG. 8). In some embodiments, the processor may be separate from the glove and connected to the glove via a multi-contact electrical connector (not shown).

The processor 150 may be configured to execute machine learning processes to train the system to recognize hand position and switch proximity in control panel training applications. The processor 150 may include a microcontroller, configurable analog and digital circuits, firmware, software, conversion formulae, lookup tables, and/or other control and measurement elements. The processor 150 may be configured to deliver an indication that a control-point activation condition has occurred. In addition, the processor 150 may transmit the identified gesture to a transceiver 130. In these embodiments, the transceiver 130 may be configured to transmit the control-point input(s) of the control-point activation condition (e.g., an identified gesture), as a message associated with control-point activation condition.

The processor 150 may include one or more cores, and each processor/core may perform operations independent of the other processors/cores. One or more of the processors may be configured with processor-executable instructions to perform operations of methods of various embodiments (e.g., methods 1400, 1500, 1600, 1700, and 1800 described herein with reference to FIGS. 11 and 15-18, respectively). The processor 150 may be any programmable microprocessor, microcomputer or multiple processor chip or chips that can be configured by software instructions (applications) to perform a variety of functions, including the functions of the various embodiments described above. In some embodiments, multiple processors may be provided, such as one processor dedicated to wireless communication functions and one processor dedicated to running other applications. Typically, software applications may be stored in internal memory before they are accessed and loaded into the processor 150. The processor 150 may include internal memory sufficient to store the application software instructions. In many embodiments, the internal memory may be a volatile or nonvolatile memory, such as flash memory, or a mixture of both. For the purposes of this description, a general reference to memory refers to memory accessible by the processor 150 including internal memory or removable memory plugged into the glove 100 and memory within the processor 150.

In some embodiments, the glove 100 may include one or more components for enabling one-way or two-way wireless communications. For example, the glove 100 may have a transceiver 160 (e.g., Bluetooth®, Zigbee®, Wi-Fi, HF, VHF, RF radio, cellular, etc.), including an antenna, for sending and receiving wireless transmissions 165, from and/or to the processor 150. The transceiver 160 may be used with the above-mentioned circuitry to implement various wireless transmission protocol stacks and interfaces.

Figure 2:
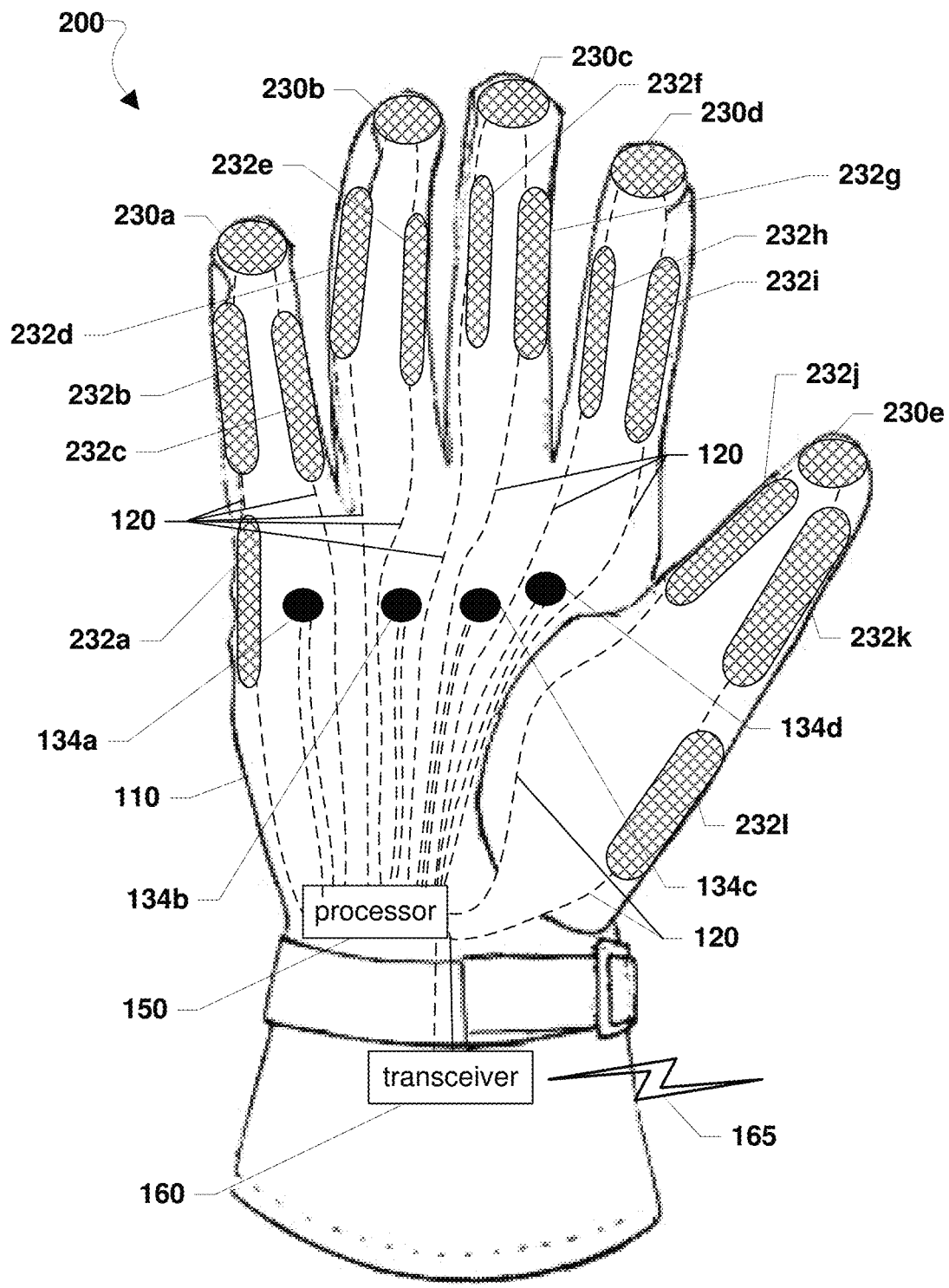
FIG. 2 is a plan view of a glove with conductive areas according to various embodiments.

FIG. 2 illustrates a glove 200 to be worn by a wearer that may be used as an input device in accordance with various embodiments. With reference to FIGS. 1-2, in some embodiments, the glove 200 may include the glove body 110, the conductive path 120, the processor 150 coupled to the conductive path 120, and may additionally include alternative expanded conductive areas 230a, 230b, 230c, 230d, 230e (i.e., 230a-230e), 232a, 232b, 232c, 232d, 232e, 232f, 232g, 232h, 232i, 232j, 232k, 232l (i.e., 232a-232l) coupled to the conductive path 120. The expanded conductive areas 230a-230e, 232a-232l may be formed as conductive pads, plates, or patches that cover a broad surface area of the glove 200 and thus reduce the size of the dead-zones, between conductive areas, in which control-point inputs will not be generated and thus control-point activation conditions cannot be detected. Since both the conductive path 120 and the expanded conductive areas 230a-230e, 232a-232l are conductive, the expanded conductive areas 230a-230e, 232a-232l provide a bigger area in which electron flows may be received and/or transmitted. In this way, the expanded conductive areas 230a-230e, 232a-232l may act like electron on-ramps to the conductive path 120. The expanded conductive areas 230a-230e, 232a-232l may be formed from low resistance meshes, inks, urethane bonded conductive fabrics, finely wound stainless steel, fabrics thinly coated with flexible conductive materials (e.g., silver), or the like.

In some embodiments, the expanded conductive areas 230a-230e, 232a-232l may be formed from higher resistance material than the conductive path 120. This combination of higher resistance and lower resistance may encourage the electrons to flow more directly from the expanded conductive areas 230a-230e, 232a-232l to the conductive path 120, following the quickest path to least resistance. In this way, higher electrical resistance areas feeding electrons into lower resistance "highways," may provide a means for location detection of a contact point on the glove.

More or fewer expanded conductive areas may be provided on the glove body 110 than illustrated in the figures. Also, each of the expanded conductive areas may be larger or smaller than illustrated in the figures. In addition, as an alternative, one or more expanded conductive areas may replace one or all of the palm conductive pads 134a-134d.

In some embodiments, substantially all of the glove body 110 may be made of conductive fabric that has a higher resistance than that of the conductive path 120. For example, the conductive path may have a resistance of 40 ohms, while the fabric of the glove body 110 may have a resistance 60-80 ohms. In this way, touching almost anywhere on the glove body 110 may be differentiated by a few ohms difference that may be detected in response to that touch. The current will follow the path of least resistance down the conductive path 120, and thus may not travel all the way down the conductive fabric of the glove body 110, with its higher resistance. In this way, the point along one particular conductive path 120, nearest to a point of contact on the conductive fabric of the glove body 110, may be considered an estimate of the control-point providing an activation condition. By using a measurement of the resistance, the processor 150 may not be able to determine precisely where the point of contact was made on the conductive fabric, but may use the estimated control-point as an indication of the general region of the glove body 110 from which the signal originated. One advantage to having providing substantially all of the glove body 110 may be made out of conductive fabric that has a higher resistance than that of the conductive path 120 is that it may eliminate dead zones on the glove body 110 in which contact does not register as an activation condition. In addition, if used in combination with imaging systems configured to take and analyze images of the glove or portions thereof (e.g., cameras on the glove or remote from the glove), the estimated control-point may be used as a confirmation or calibration between two different tracking systems. Further, the timing of the detected activation condition from the estimated control-point, the estimated control-point location, and any other activation condition detection input (e.g., from another tracking system, such as an imaging system) may be used for machine learning to train machine learning models to more accurately correlate control-point activation conditions with a precise contact timing and/or glove location, orientation, and/or motions.

In addition, if the wearer slides a glove-finger along a portion of the higher resistance conductive fabric, but maintaining engagement therewith, the continuous signal with changing resistance may represent control-point activation conditions associated with a slider or potentiometer operations, such as for scrolling, zooming in/out, or other functions.

In some embodiments in which substantially all of the glove body 110 is made out of conductive fabric, providing dual resistive/capacitive conductive pads (e.g., in the expanded conductive areas 130a-130e, 132a-132g, and 134a-134d), may enable control-point inputs to be generated from almost anywhere on the entire glove 100. For example, with reference to FIG. 1, by touching the glove body 110 at a particular location, such as the control-point CP, a resistance or capacitance measurement (depending on the type of conductive pad) taken from a conductive pad at the expanded conductive area 132e may be different from that taken at expanded conductive area 134d or 130d. Comparing measurements from these two neighboring conductive pads may be used to approximate the location of the control-point CP, knowing that measurements from the further conductive pad will tend to give a higher resistance value. Similarly, touching directly in between two conductive pads may yield equal resistance values, indicating the tough-point is equidistant from those conductive pads. In addition, a third conductive pad may be used in this way to triangulate and determine a more precise location of control-point CP.

Figure 3A:
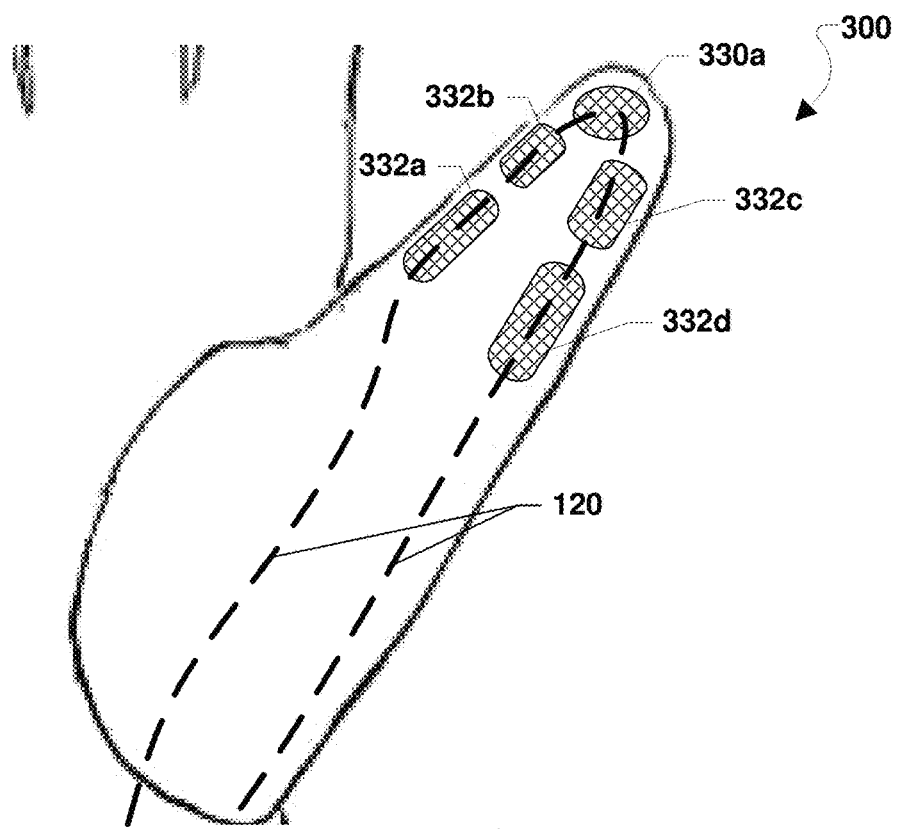
FIG. 3A is plan view of a thumb portion of a glove with a conductive path extending through a central portion of various conductive areas according to various embodiments.

FIG. 3A illustrates the conductive path 120 along a thumb portion of a glove 300 in accordance with various embodiments. With reference to FIGS. 1-3A, in some embodiments, the conductive path 120 may extend across a longest extent of each or most of the expanded conductive areas 330a, 332a, 332b, 332c, 332d. This configuration may ensure the expanded conductive areas 330a, 332a, 332b, 332c, 332d maintain contact with at least a portion of the conductive path 120.

Figure 3B:
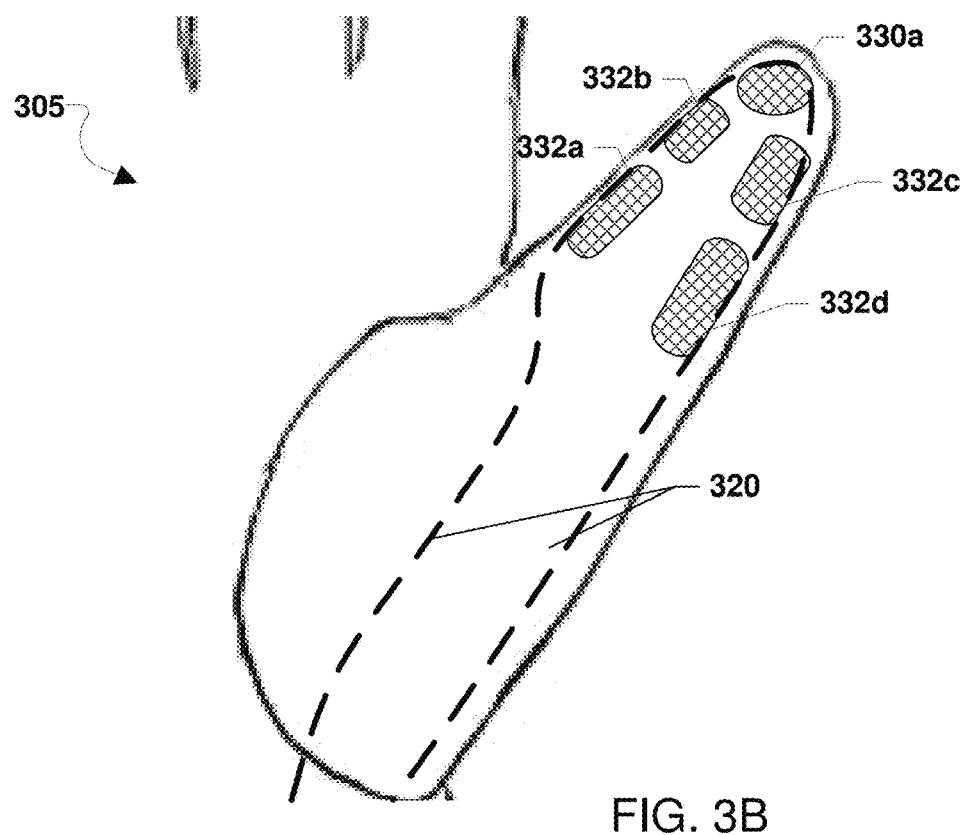
FIG. 3B is plan view of a thumb portion of a glove with a conductive path extending through an outer portion of various conductive areas according to various embodiments.

FIG. 3B illustrates an alternative conductive path 320 along a thumb portion of a glove 305 in accordance with various embodiments. With reference to FIGS. 1-3B, in some embodiments, the conductive path 320 need not extend across a central or longest extent of the expanded conductive areas 330a, 332a, 332b, 332c, 332d. Rather, the conductive path 320 may contact the expanded conductive areas 330a, 332a, 332b, 332c, 332d along an edge or almost any portion thereof, such as fabric seams and/or the outer edges shown in FIG. 3B. The conductive path 320 may only need to contact a portion of each of the expanded conductive areas 330a, 332a, 332b, 332c, 332d in order to effectively and reliably conduct electrons. Thus, the conductive path 320 may be routed in such a way as to still contact the expanded conductive areas 330a, 332a, 332b, 332c, 332d while avoiding seams and/or areas that might cause user discomfort, and without restricting or hindering free movement of the glove 305. In this way, the conductive path 320 may provide ergonomic benefits while still providing a continuous loop extending away from and back to the processor (e.g., 150) for conveying inputs from the expanded conductive areas 330a, 332a, 332b, 332c, 332d. Additionally, the expanded conductive areas may be shaped in such a way as to allow the conductive path to be hidden within seams of fabric or via other methods. In this way, the expanded conductive areas may extend over into fabric seams and still maintain contact with the conductive path 320 within the seam.

Figure 4A:
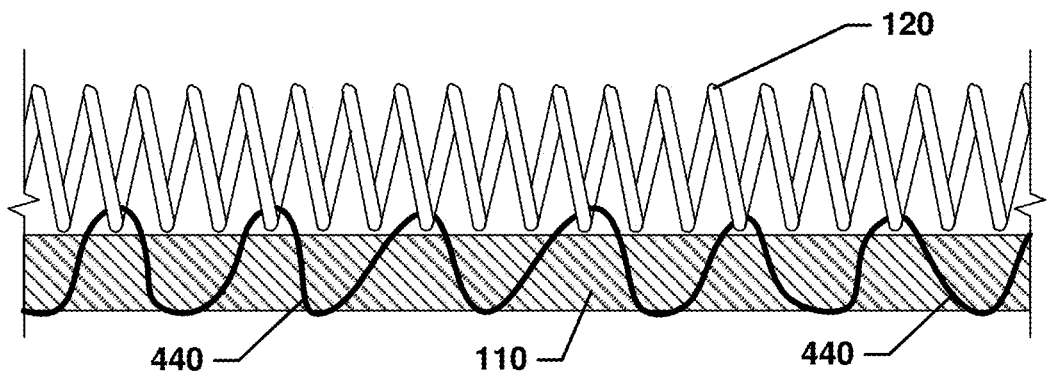
FIG. 4A is a cross-sectional view of conductive thread used in conjunction with coiled wire to form a conductive path according to various embodiments.
Figure 4B:
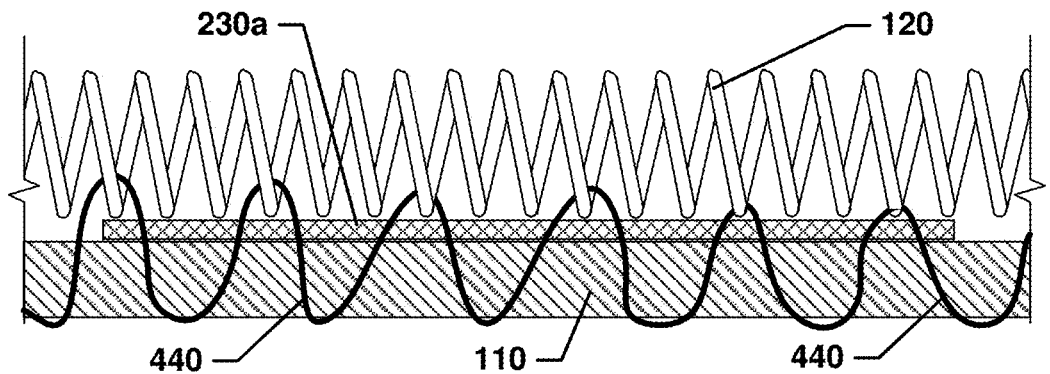
FIG. 4B is a cross-sectional view of conductive thread used in conjunction with coiled wire and a conductive area material according to various embodiments.

FIG. 4A illustrates a cross-sectional view of a conductive thread 440 used in conjunction with a coiled wire forming the conductive path 120 in accordance with various embodiments. With reference to FIGS. 1-4A, in some embodiments, the conductive thread 440 may be used to stitch the conductive path 120 (i.e., the coiled wire) to the glove body 110. In this way, the conductive thread 440 maintains contact between the conductive path 120 and the fabric of the glove body 110. In addition, the conductive thread 440 may act as a failsafe for the electric conductivity of the conductive path 120 in case there is a break therein. The conductive path 120, which may be a metal coil spring, may eventually fatigue from repeated flexing of the metal. In this way, the conductive path 120 may be provided as a primary means of conductivity, while the conductive thread 440 may be provided as a secondary means of conductivity across the glove.

With reference to FIGS. 1-4B, in some embodiments, the conductive thread 440 may be used to stitch not only the conductive path 120 (i.e., the coiled wire) to the glove body 110, but also a pad forming the expanded conductive area 230a there between. In this way, the conductive thread 440 maintains contact between the conductive path 120, the expanded conductive area 230a, and the fabric of the glove body 110.

Figure 5:
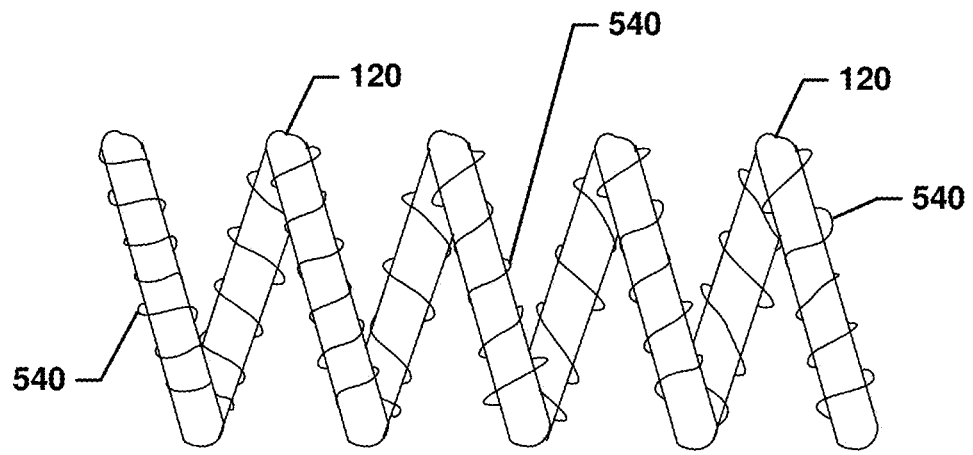
FIG. 5 is a side view of a coiled wire forming a conductive path with a conductive thread used to reinforce and provide a conductivity backup according to various embodiments.

FIG. 5 illustrates a side view of a coiled wire forming a conductive path with a conductive thread used to reinforce and provide a conductivity backup in accordance with various embodiments. With reference to FIGS. 1-5, in some embodiments, a conductive thread 540 may be concentrically wrapped around the conductive path 120, forming a redundancy or "bridge" in the event a break forms in the conductive path 120. Optionally, a further fabric thread may be used to secure the conductive path 120 wrapped by the conductive thread 540 to the glove body (e.g., 110).

Figure 6:
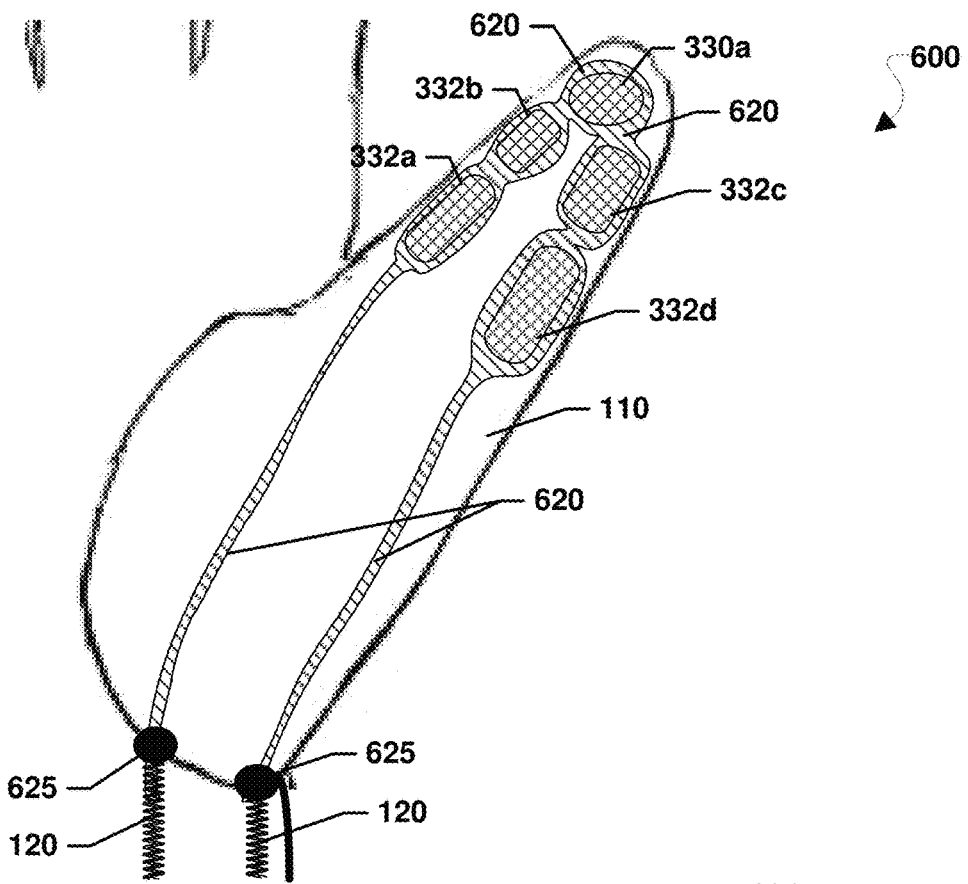
FIG. 6 is plan view of a thumb portion of a glove with a conductive path formed by conductive ink according to various embodiments.

FIG. 6 illustrates a conductive path 620 formed by conductive ink along a thumb portion of a glove 600 in accordance with various embodiments. With reference to FIGS. 1-6, in some embodiments, conductive ink may replace the coiled wire described in other embodiments to form the conductive path 620, according to various embodiments. The conductive ink may be printed directly onto the glove body 110. Some conductive inks are not only flexible but even stretchable, making them more easily integrated into clothing, such as a glove. For example, DuPont' (DuPont de Nemours, Inc., Wilmington, DE) markets a printable ink under the brand name Intexar™ that may provide a thin, form-fitting circuit that can be seamlessly fused with standard fabrics, allowing for unprecedented comfort and freedom in wearable electronics design.

The conductive path 120 may include portions of conductive ink and other portions of other conductive material, such as coiled wire. For example, coiled wire may secure directly to the processor, providing fly leads that may be secured to the conductive ink. The coiled wire may be sewn, bonded (e.g., by soldering or with conductive paste), or otherwise secured to the conductive ink of the conductive path 620 at one or more appropriate attachment locations 625. Alternatively, the conductive ink may extend from the processor (e.g., 150), to a distal-most expanded conductive area 330a, and loop back to the processor, surrounding any expanded conductive areas 332a, 332b, 332c, 332d along the way.

The conductive path 620 may widen in locations in which the expanded conductive areas 330a, 332a, 332b, 332c, 332d are disposed. In this way, each of the expanded conductive areas 330a, 332a, 332b, 332c, 332d may be surrounded by conductive material, namely the conductive ink.

Various embodiments may include a conductive wire, buried under the conductive ink as a redundancy or "bridge" in the event of cracks or breaks in the printed ink. In this way, the wire and/or the conductive ink may serve as a primary conductor and the other serves as a secondary conductor.

Various embodiments may include an encapsulant over the conductive ink. The encapsulant may be a non-conductive layer of material, such as polyurethane, that covers the conductive ink to reinforce and/or provide extra strength thereto. In addition, the encapsulant may cover areas of the ink not intended to be exposed. The encapsulant may protect the integrity of the conductive ink and be provided as a separate graphics layer.

Figure 7:
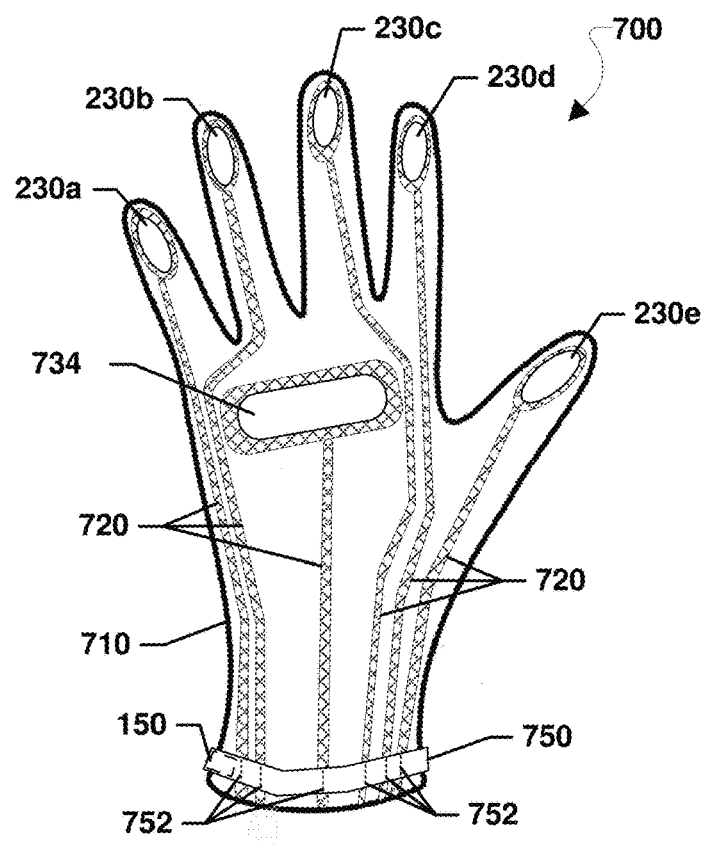
FIG. 7 is plan view of a glove with a conductive path formed by conductive ink printed onto a glove body formed as a surgical glove according to various embodiments.

FIG. 7 illustrates a glove 700 including a conductive path 720 formed by conductive ink printed onto a glove body formed from a unitary thin elastic polymer, such as a latex, nitrile rubber, polyvinyl chloride, neoprene or other surgical or medical glove material in accordance with various embodiments. With reference to FIGS. 1-7, in some embodiments, the glove 700 may include a glove body 710, a conductive path 720, and the processor 150 coupled to the conductive path 720 through a control strap 750. In addition, the glove 700 may include expanded conductive areas 230a-230e, 734, which may be bonded with conductive adhesive to the glove body 710 over widened portion of the conductive path 720. For example, the expanded conductive areas 230a-230e, 734 may be applied as stickers or labels over the widened portions of the conductive path 720. The conductive path 720 may be similar to the conductive path 620 described above with regard to the glove 600. Alternatively, sensors or switches may be substituted for the expanded conductive areas 230a-230e. Forming the glove body 710 from a unitary thin elastic polymer material may minimize costs for one of the most extensive materials forming the glove 700. This combined with the easy-to-assemble and relatively low cost conductive paths 720 and expanded conductive areas 230a-230e, 734 may help keep overall production costs low. Enabling the production of a low-cost version of the glove 700 may enable use as a disposable glove, such as in medical or other single/limited-use settings.

The control strap 750 may be a separate removable element configured to be mounted onto a wrist portion of the glove 700. In this way, the glove 700 may be disposable and replaced with a fresh glove 700, while the control strap 750 may be transferred to the fresh glove 700 and thus reused. For example, the control strap 750 may include conductive contact strips 752 configured to align with and engage individual branches of the conductive path 720 at the wrist region. When strapped firmly around the wearer's wrist, the control strap 750 may force the conductive contact strips 752 into engagement with the wrist portions of the conductive path 720. The control strap 750 may additionally include a transceiver and circuitry for wireless communications.

Figure 8:
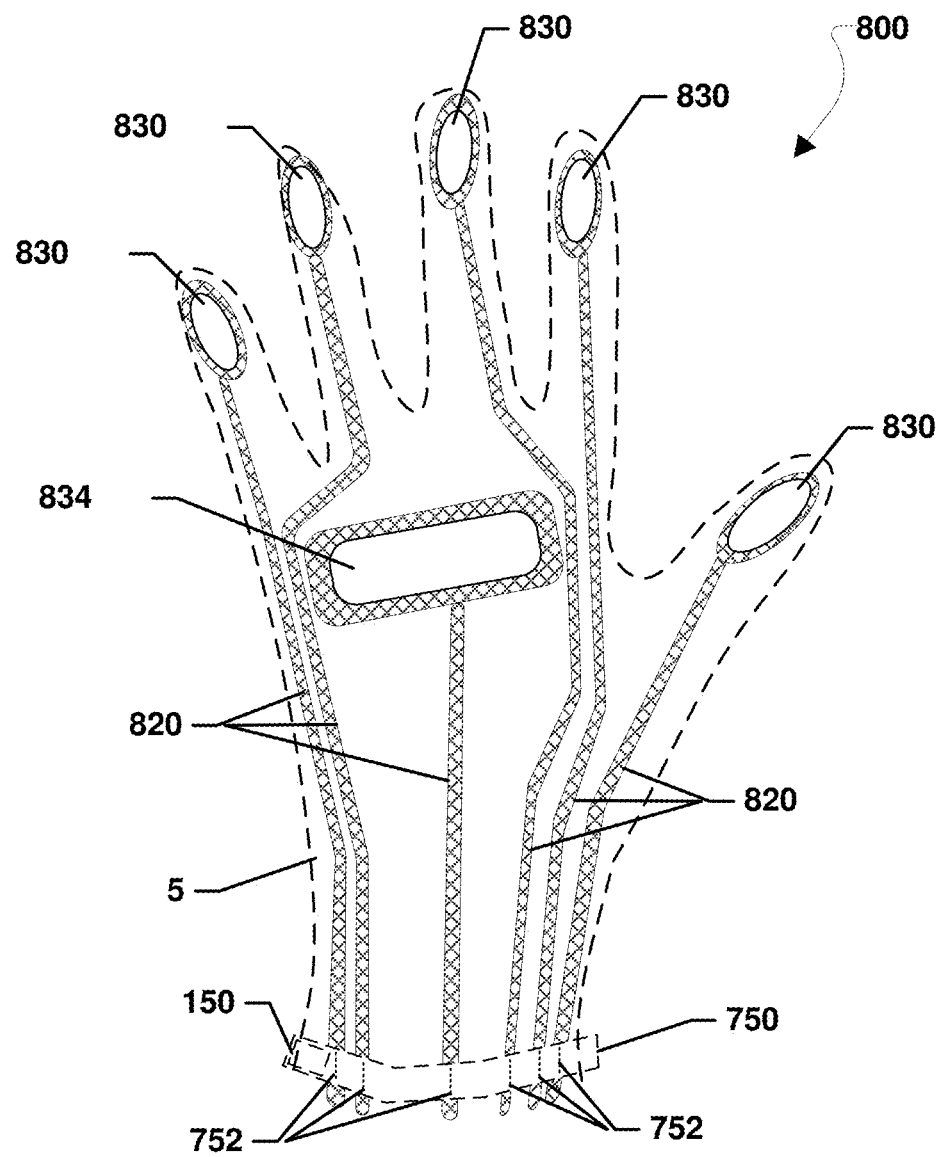
FIG. 8 is plan view of a conductive sticker set formed from conductive material carried by an adhesive substrate according to various embodiments.

FIG. 8 illustrates a conductive sticker set 800 for application to a hand 5 or wearable surface in accordance with various embodiments. With reference to FIGS. 1-8, in some embodiments, the conductive sticker set 800 may include elements similar to those described for the glove 700 in FIG. 7. In fact, the conductive sticker set 800 may be applied to a prefabricated glove body (e.g., 710) or even directly to a user's hand. The conductive sticker set 800 may include a conductive path 820 and expanded conductive areas 830, 834, which all may be carrier on an adhesive substrate. Before application to the hand or glove, a removeable backing may be peeled off the adhesive substrate to expose a back-side thereof that is configured to adhere to the hand or glove. The conductive path 820 and expanded conductive areas 830, 834 may be printed onto the adhesive substrate and carrier thereon for transfer to the hand or glove in accordance with various embodiments.

Similar to the glove 700, the conductive sticker set 800 may be configured to work in conjunction with the control strap 750 that may house a processor (e.g., 150) and optionally a transceiver (e.g., 160). The control strap 750 may include conductive contact strips 752 configured to align with and engage individual branches of the conductive path 820 at the wrist region. When strapped firmly around the wearer's wrist, the control strap 750 may force the conductive contact strips 752 into engagement with the wrist portions of the conductive path 820.

FIG. 9 illustrates a glove 900 including wrist-mounted cameras and optional surface markers for tracking movement and position of portions of the glove 900 in accordance with various embodiments. With reference to FIGS. 1-9, in some embodiments, one or more wrist-mounted cameras 970 may be mounted on a wrist portion of the glove body, such as on the control strap 750 thereof. For example, four separate wrist-mounted cameras 970 may be included that are distributed on the control strap 750 in such a way as to be evenly distributed around the wearer's wrist when worn. In the orientation shown in FIG. 9, three of four wrist-mounted cameras 970 are shown. More wrist-mounted cameras 970 may be included and as few as one wrist-mounted camera 970 may be included for embodiments using wrist-mounted cameras. The one or more wrist-mounted cameras 970 may be configured to provide imaging to a processor (e.g., 150), which may be housed in a control module 950 elsewhere on the glove. Alternatively, the processor may be located, alongside one or more of the wrist-mounted cameras 970, on the control strap 750. The processor may be used to analyze images for detecting or translating finger movements relative to a palm portion of the glove 900 or other fingers thereof. In addition, the one or more wrist-mounted cameras 970 may be used to detect the touching or approaching of a control surface (e.g., switch, knobs, etc.) and/or other portions of the glove 900.

In various embodiments, portions of the glove, such as the finger tips/sides or back/palm, may optionally include imprinted markers A, B, C, D, E, such as bar codes, QR codes, or other unique symbols, which may be readily identifiable from images taken by the one or more wrist-mounted cameras 970. A greater or fewer number of imprinted codes may be included on the glove 900. FIGS. 9B-9F illustrate relief views of the imprinted markers A, B, C, D, E shown in FIG. 9. Distinct markers on the glove, particularly on the fingers and hand may make it easier for the wrist-mounted cameras 970 to detect finger and thumb movements. In some embodiments, the imprinted markers A, B, C, D, C may include LEDs emitting light (e.g., infrared light) in patterns that are distinct to the camera systems. The LEDs may be mounted on extended conductive areas or directly on a conductive path.

The glove 900 may otherwise have aspects of one or more of the gloves 100, 200, 300, 305, 600, 700 described above with respect to other embodiments. In this way, the wrist-mounted cameras 970 may not only provide a visual indication of glove finger position and orientation, but also have a calibration input for the image tracking from the conductive surfaces/paths used to detect control-point activation conditions, described above with regard to the conductive paths and expanded conductive areas. Alternatively, the conductive surfaces/paths may provide the main control-point activation detection, with the visual indications from the wrist-mounted cameras 970 providing the calibration input. This calibration between two different tracking systems may provide an especially powerful and accurate technique for tracking finger movements, particularly of the thumb. Additionally, thumb touch locations on fingers can be tuned and tracked using kinematic models.

FIGS. 9B-9F illustrate relief views of various glove markers shown on the glove 900 in FIG. 9A in accordance with various embodiments. With reference to FIGS. 1-9F, in some embodiments, the glove markers may be reflective in order to be more easily tracked by the camera system. Alternatively, or additionally, one or more control surfaces (e.g., switch, knobs, etc.) may include imprinted markers similar to those described above. The imprinted markers on the one or more control surfaces may help the processor determine or confirm a position or movements of the fingers and hand relative to the one or more control surfaces.

Figure 10:
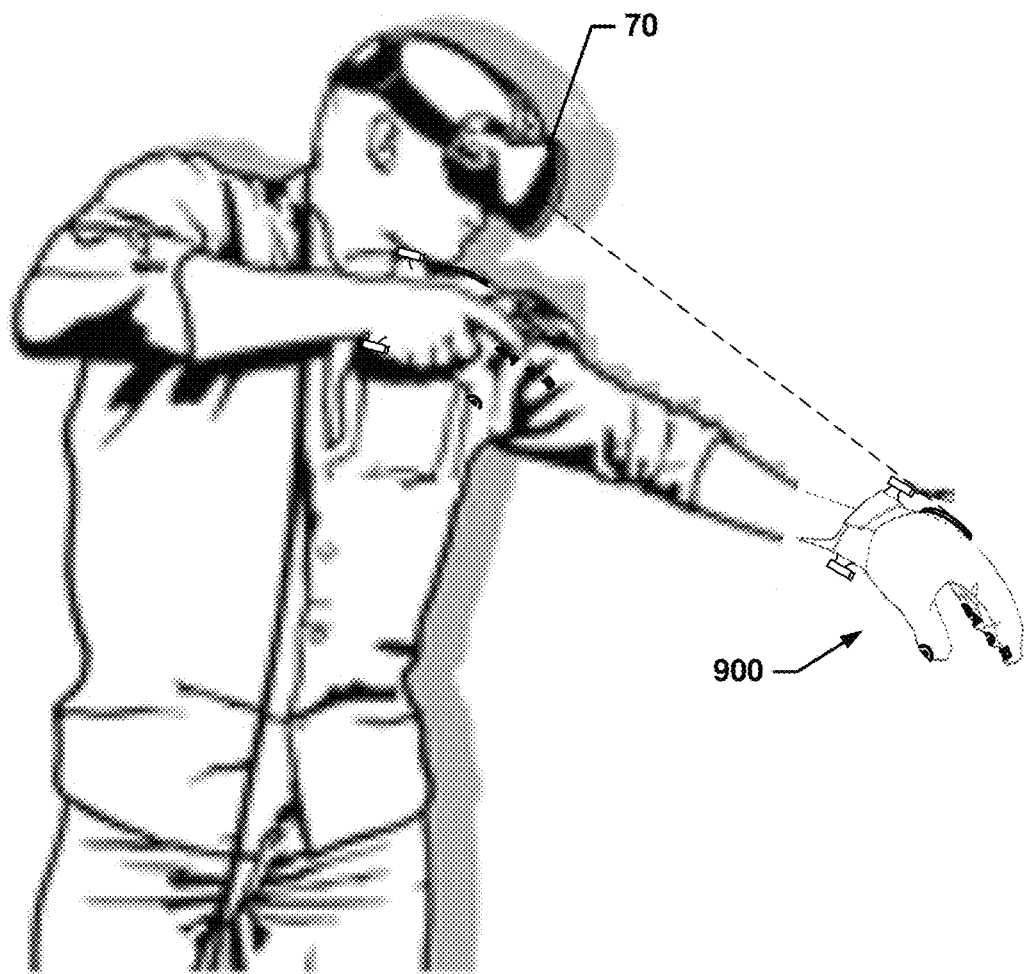
FIG. 10 is an illustration of a wearer wearing the glove in FIG. 9A in conjunction with a headset camera according to various embodiments.

FIG. 10 illustrates the glove 900 in FIG. 9A used in conjunction with a headset camera 70 for analyzing characteristics, movement, and position of the glove 900 in accordance with various embodiments. With reference to FIGS. 1-10, in some embodiments, imaging from the headset camera 70 may be used in conjunction with or in place of imaging collected from the wrist-mounted cameras 970 or other cameras for making determinations about glove position, size, orientation, and/or control-point activation conditions.

Figure 11:
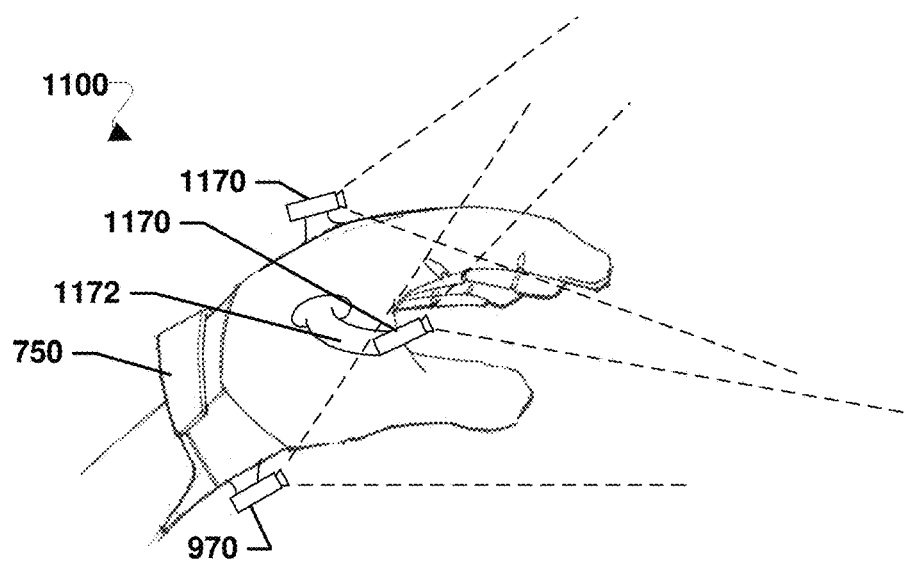
FIG. 11 is a side view of a glove with glove-mounted cameras according to various embodiments.

FIG. 11 illustrates a glove 1100 including glove-mounted cameras for tracking movement and position of portions of the glove 1100 in accordance with various embodiments. With reference to FIGS. 1-11, in some embodiments, one or more glove-mounted cameras 1170 may be mounted on or supported by various portions of the glove body, such as on the back-of-the-hand or side portions of the glove 1100. In addition, one or more wrist-mounted cameras 970 may also optionally be included, as described above with regard to glove 900. Alternatively, the glove-mounted cameras 1170 may support arms 1172 extending from a portion of the glove in order to elevate and/or properly orient the cameras relative to the glove. For example, the support arms 1172 may wrap around the glove, like one or more curved horns, toward a palm-side of the glove, which may position the glove-mounted cameras 1170 for capturing images of the palm and/or the underside of the fingers (e.g., the finger tips). In this way, the glove-mounted cameras 1170 may be positioned as needed, including with extending support arms, in order to obtain the desired perspective for imaging to capture a full range of movements and orientations of the glove and portions thereof. Unlike the wrist-mounted cameras 970, the glove-mounted cameras 1170 avoid the added articulate that may occur between the wrist and hand.

As an alternative the gloves 900, 1100 may be made as fingerless gloves, since the cameras (e.g., 970, 1170) may be used to track finger-tip movements and thus detect control-point activation conditions.

When a conductive area of the glove, such as a conductive pad, is brought into contact with or gets within close proximity to one another, a signal may be generated indicative of a gesture being formed by the user wearing the glove. For example, when the glove is formed into a fist gesture by the user's hand, certain conductive pads located in finger tips, along the thumb, and within the palm of the glove may be brought into contact or within close proximity Circuit(s) established based on this contact or close proximity may generate a signal indicative of the fist gesture. In some embodiments, such generated signal may be carried via circuitry within the glove.

Figure 12:
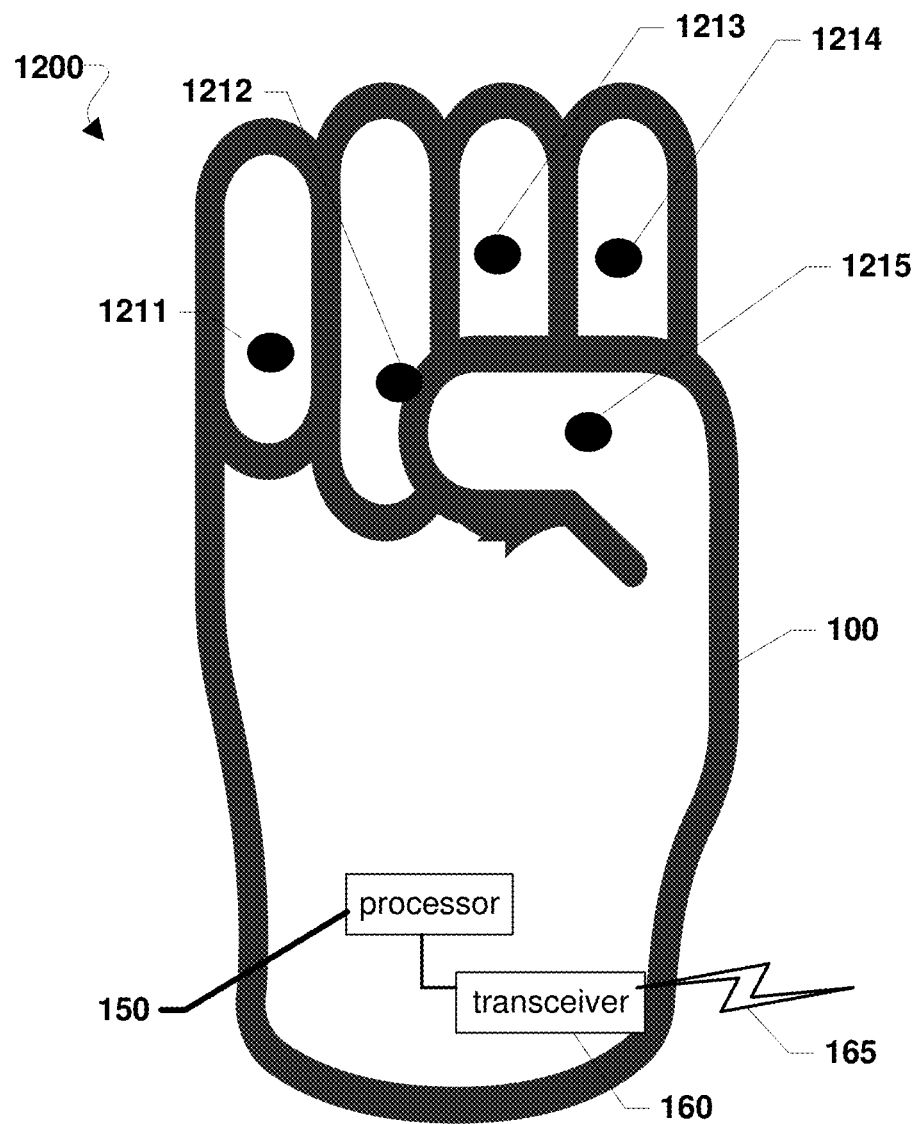
FIG. 12 is a schematic illustration of a gesture made by a wearer with a glove according to various embodiments.

FIG. 12 illustrates an example gesture 1200 formed by a glove 100 according to various embodiments. The gesture 1200 is a clenched fist. With reference to FIGS. 1-12, the glove 100 may include sensors 1211, 1212, 1213, 1214, 1215 located along a back side of each finger portion, including the thumb. Although not explicitly shown in FIG. 12, when gesture 1200 is formed, the sensors 1211, 1212, 1213, 1214, 1215 may come into close proximity with other sensors located in the palm area of the glove. In addition, thumb sensor 1215 may come in contact with or close proximity to one of the other sensors 1211, 1212, 1213, 1214, 1215. Two sensors or expanded conductive areas coming in contact with one another may close a circuit and thus generate a signal that the event has occurred. Similarly, two or more sensors coming into close proximity of one another may be detectable by the sensors 1211, 1212, 1213, 1214, 1215 and thus generate a signal that the event (e.g., a fist gesture was made) has occurred. The generated signal may be carried via circuitry or the conductive path to the processor 150 and/or the transceiver 160.

Figure 13A:
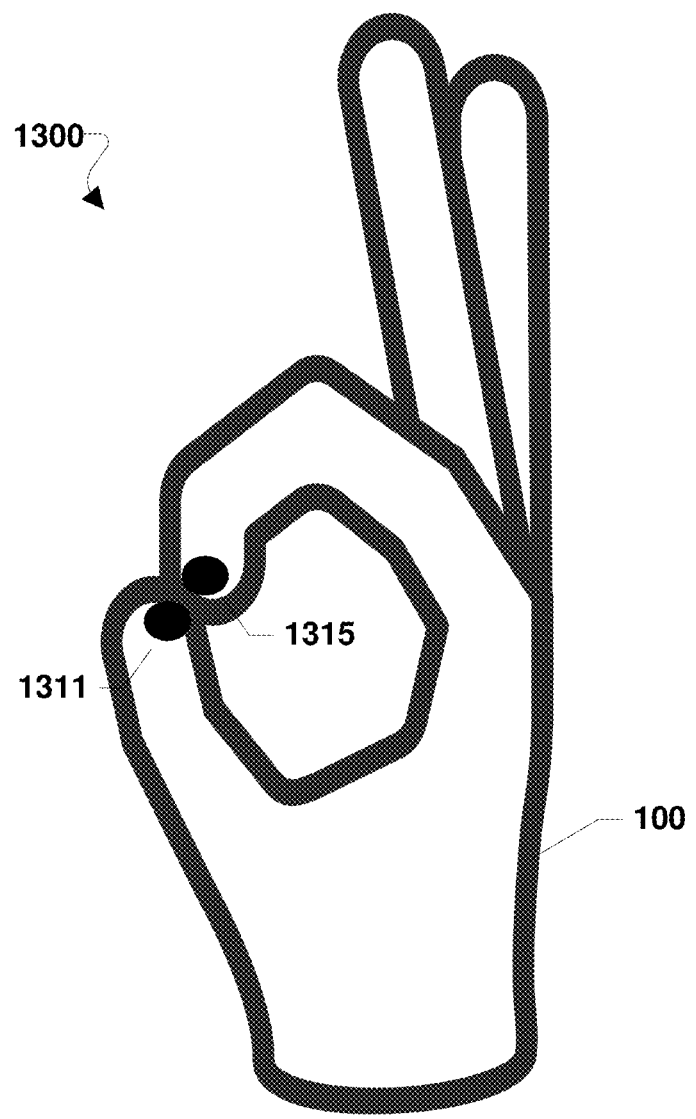
FIG. 13A is a schematic illustration of another gesture made by a wearer with a glove according to various embodiments.

FIG. 13A illustrates an example gesture 1300 formed by the glove 100 according to various embodiments. With reference to FIGS. 1-13, when sensor 1311 is brought into contact with or within close proximity to sensor 1315, a circuit may be formed that may generate a signal indicative of the gesture 1300.

Figure 13B:
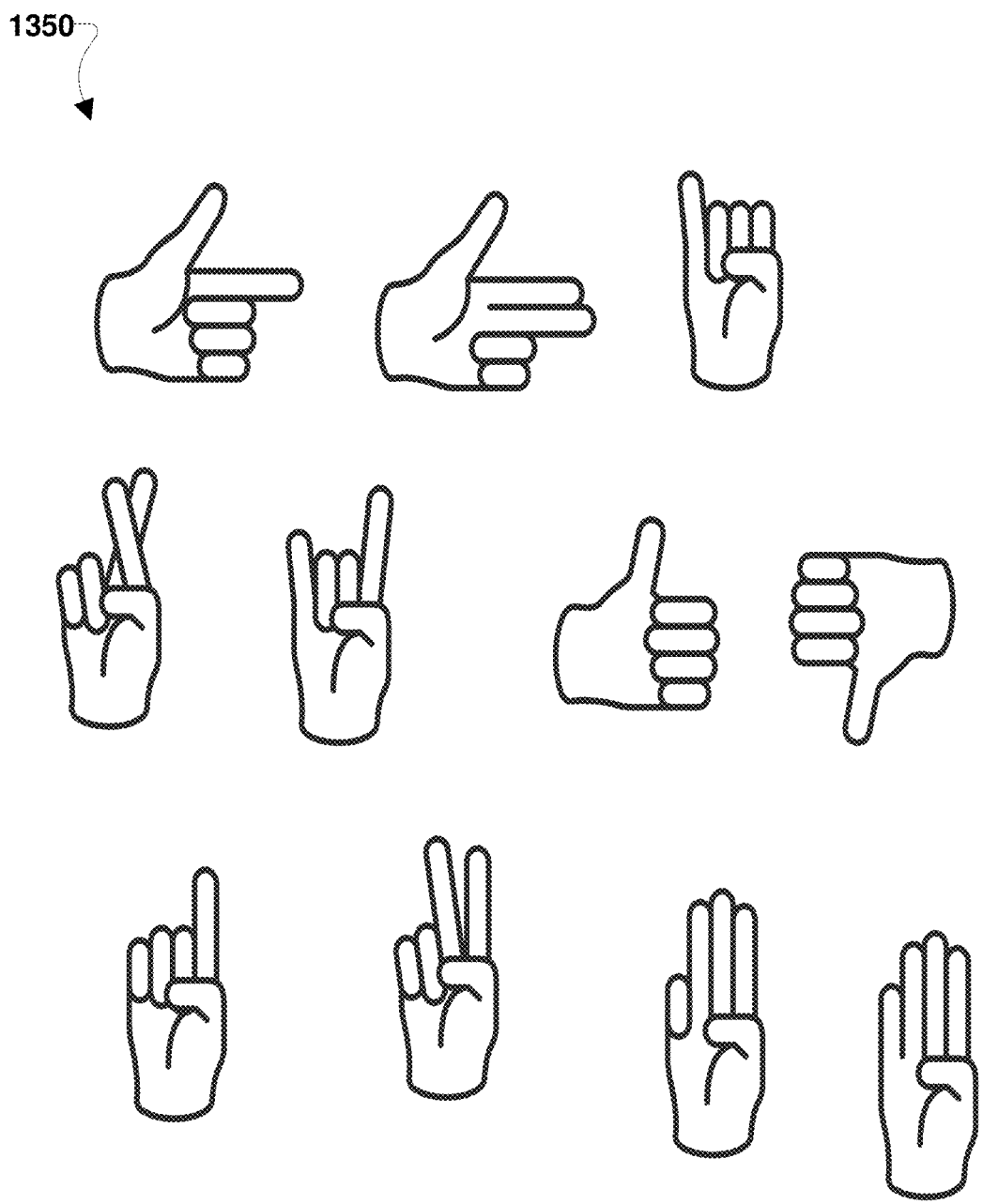
FIG. 13B is a schematic illustration of numerous different gestures made by a wearer with a glove according to various embodiments.

FIG. 13B illustrates various example gestures 1350 formed by a glove according to various embodiments.

In various embodiments, the glove (e.g., 100, 200, 300, 305, 600, 700, 900, 1100) and other input devices (e.g., control panel surfaces) may be used to detect control-point activation conditions associated with glove touches that generate control-point inputs. For example, when two conductive portions of the glove touch or when a conductive portion of the glove touches a conductive control panel surface separate from the glove control-point inputs may be generated, received by a processor (e.g., 150) and analyzed to determine whether a control-point activation condition exists. A processor in the glove may control its own control-point activation condition detection system. In addition, the control panel, which is remote from the glove, may optionally include its own control-point activation condition detection systems. In yet further embodiments, the glove and/or the control panel may transmit received control-point inputs, as a message associated with the control-point activation condition, to a remote computing device for processing and running control-point activation condition detection systems.

Figure 14:
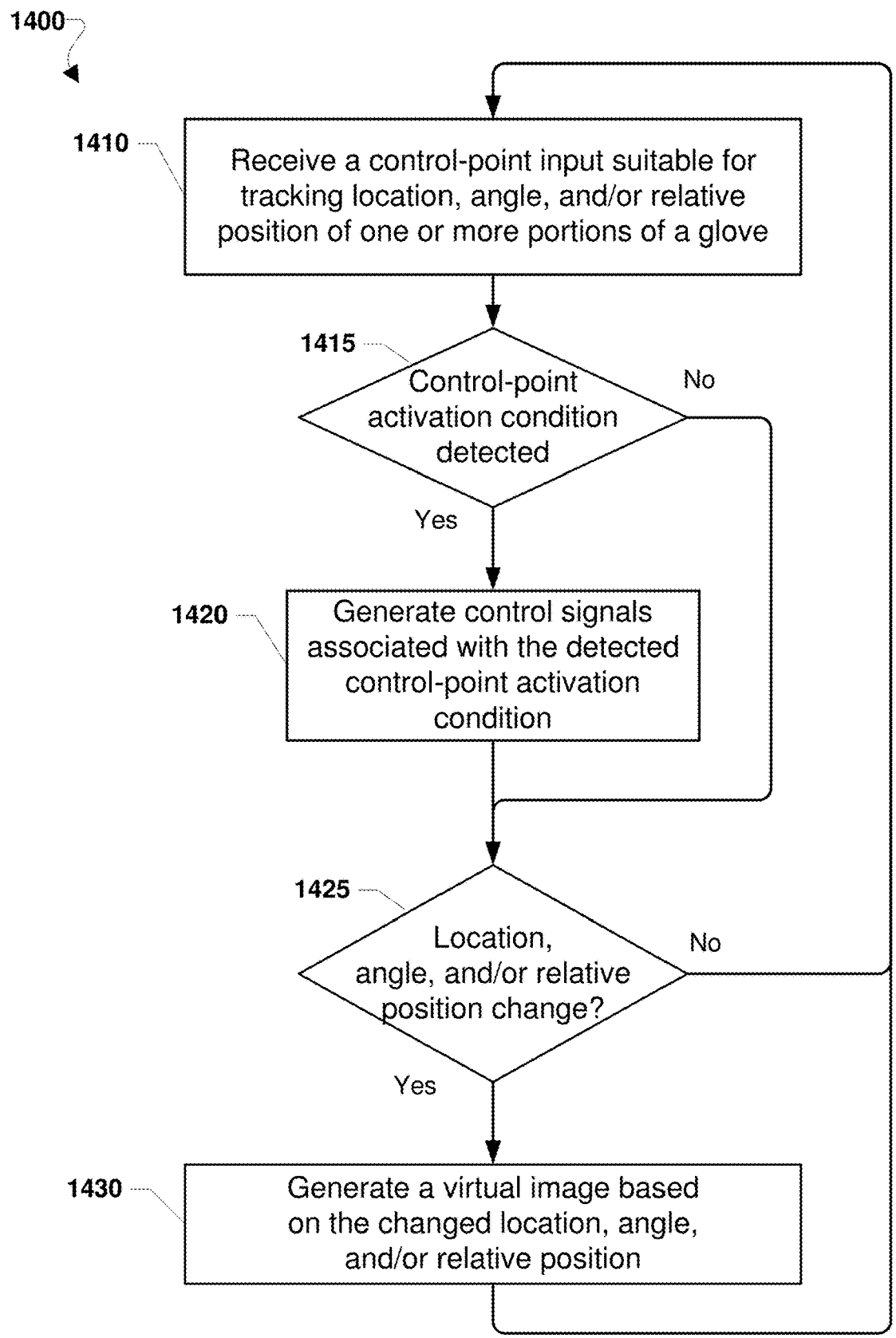
FIG. 14 is a process flow diagram of a method of control-point activation detection for generating control signals according to various embodiments.

FIG. 14 illustrates an example method 1400 for control-point activation detection for generating control signals based on particular glove positions, orientations, and/or movements, that may be implemented in a processor or computing device coupled to a glove (e.g., 100, 200, 300, 305, 600, 700) according to various embodiments. With reference to FIGS. 1-14, the method 1400 may be performed by a processor, such as a processor (e.g., 150) in the glove (e.g., 100, 200, 300, 305, 600, 700, 900, 1100) or another computing device (e.g., 1900 illustrated in FIG. 19). For ease of reference, the device executing operations of the method 1400 is referred to herein generally as a "processor."

In block 1410, the processor may receive a control-point input suitable for tracking location, angle, and/or relative position of one or more portions of a glove. The glove position information may come from a control-point input, such as from conductive pads or other conductive materials on the glove or a control panel, sensors, imaging data, or other inputs associated with tracking location, angle, and/or relative position of one or more portions of the glove.

The control-point input may be received in response to a wearer of the glove causing one or more control-point activation conditions to occur, such as by forming a gesture or interacting with a control surface remote from the glove. For example when forming a gesture, a wearer may bring two or more portions of the glove, such as the expanded conductive areas (e.g., 130a-130e, 132a-132g, and 134a-134d), conductive path (e.g., 120) or other conductive areas of the glove into contact or close proximity with one another, which may generate a control-point input signal. In this way, forming gestures such as a fist, an "OK" sign, a "V" for victory sign, pointing using an index finger, a thumbs up/down gesture, or any of various other static or dynamic gestures may cause control-point inputs to be generated. Similarly, just moving the glove and orienting the glove in a particular way may be detected by inertial or other sensors, which may generate a control-point input signal.

Alternatively, the control-point input information may be received in response to a wearer of the glove moving and/or positioning the glove, but not actually causing a control-point activation condition. This may occur when the wearer moves the glove between gestures, does not intend to form a recognized gesture, or otherwise moves or arranges the glove without causing a control-point activation condition.

Circuitry connected to the expanded conductive areas may convey an electron flow (i.e., a signal) from points of contact in the expanded conductive areas to the processor. In some embodiments, the signal may be indicative of the gesture being formed. In some embodiments, the signal may be an indication of which two or more expanded conductive areas were brought into contact or close proximity. In some embodiments, the signal may provide an indication of a location of the contact or close proximity. In some embodiments, the signal may include multiple signals. For example, when a formed gesture brings multiple pairs or combinations of expanded conductive areas into contact or close proximity, each pair or combination of areas may convey a separate signal and these signals may be combined or otherwise collected into the signal received by the processor.

In some embodiments, one or more sensors may be used to generate signals suitable for tracking location, angle, and/or relative position of one or more portions of a glove. For example, using camera imaging or gyroscopic sensor data, a thumbs up or thumbs down gesture may be detected, which both include a similar gesture but with different hand orientations. The generated signal may not only include an indication of hand orientation, but also include hand motion and/or acceleration for identifying dynamic gestures. For example, an open palm being brought down into a fist may represent an instruction to stop. In this way, in addition to static hand gestures, a multitude of dynamic gestures may be used/detected. The signals received from sensors may also be received as glove position information suitable for tracking location, angle, and/or relative position thereof.

In determination block 1415, the processor may determine whether a control-point activation condition is detected. In particular, the processor may determine whether the received control-point input matches an input associated with a control-point activation condition. There may be many control-point activation conditions, each associated with functions or commands used in a VR application and each one may be associated with a particular one or more control-point inputs. If the received control-point input matches those of one of the control-point activation conditions, then the corresponding control-point activation condition has been detected. Otherwise, if the received control-point input does not match any inputs associated with a control-point activation condition, then no control-point activation condition has been detected. Thus, in response to a control-point activation condition being detected (i.e., determination block 1415="Yes"), the processor may generate control signals associated with the detected control-point activation condition in block 1420.

In determination block 1425, following the generation of control signals in block 1420 or in response to the determination that control-point activation condition is detected in determination block 1415, the processor may determine whether a location, angle, and/or relative position of the one or more portions of the glove have changed.

In response to determining that the location, angle, and/or relative position of the one or more portions of the glove have changed (i.e., determination block 1425="Yes"), the processor may generate a virtual image based on the changed location, angle, and/or relative position. The processor may treat circumstances in which no previous virtual image has been generated because the virtual imaging process has just begun as the location, angle, and relative position having changed. In response to determining that none of the location, angle, or relative position of the one or more portions of the glove have changed (i.e., determination block 1425="No") or following the generation of the virtual image in block 1430, the processor may await receipt of a further control-point input so the process of the method 1400 may start again in block 1410.

In various embodiments, the glove (e.g., 100, 200, 300, 305, 600, 700, 900, 1000 and related control-point activation detection systems may be used to train a processor (e.g., 150) to not only detect touch-type control-point activation conditions but also non-contact control-point activation conditions, such as hovering or other non-contact gestures. Using machine learning the processor may be "trained" to more accurately determine glove position, orientation, and movements or better recognize control-point activation conditions. The processor may be trained to detect a precise moment of contact with a control panel remote from the glove, such as in a mock-up cockpit. Not only may the processor learn how to deal with unique instrument panels, but also different users (i.e., glove wearers) may orient their hands differently depending on the proximity of the control panel to that user. For example, a user may orient their hand one way when interacting with a control panel switch that is located far away from the user and orient that hand differently when interacting with a different control panel switch or one that is much closer.

Figure 15:
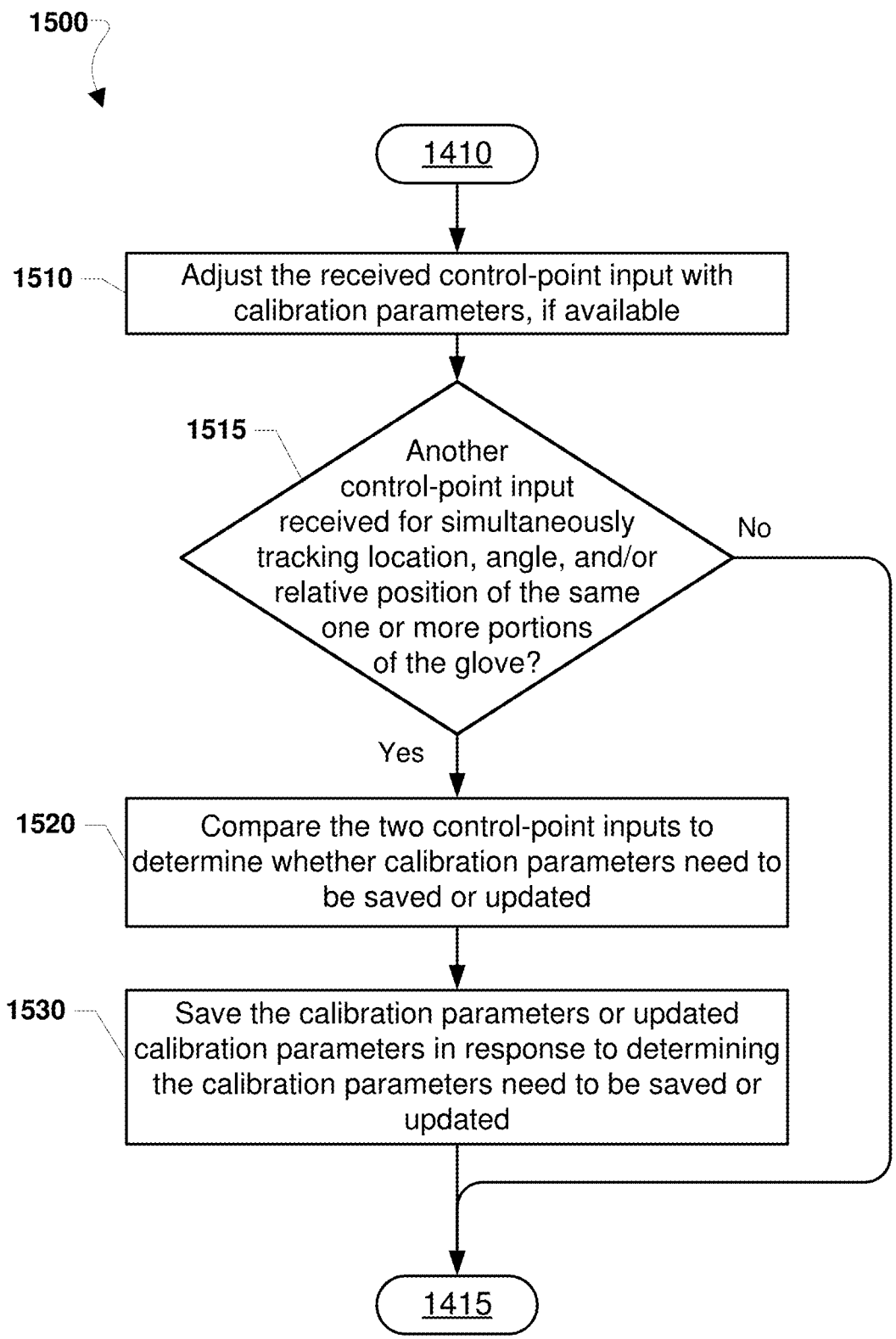
FIG. 15 is a process flow diagram of a method of control-point activation detection for generating control signals according to various embodiments.

FIG. 15 illustrates an example method 1500 that may be implemented in a processor or computing device coupled to a glove (e.g., 100, 200, 300, 305, 600, 700), which may be performed as part of the method 1400 for control-point activation detection for generating control signals according to various embodiments. With reference to FIGS. 1-15, the method 1500 may be performed by a processor, such as a processor (e.g., 150) in the glove (e.g., 100, 200, 300, 305, 600, 700) or another computing device (e.g., 1900 illustrated in FIG. 19). For ease of reference, the device executing operations of the method 1500 is referred to herein generally as a "processor."

In some embodiments following the operations of block 1410 of the method 1400 (FIG. 14), in block 1510, a processor may adjust the received control-point input with calibration parameters, if available. The calibration parameters may be determined using at least two control-point inputs previously received for simultaneously tracking and comparing the same location, angle, or relative position of the same one or more portions of the glove. For example, one control-point input may be received when two conductive portions of a glove make contact or a conductive portion of the glove makes contact with a conductive surface of a control panel remote from the glove. In addition, a second control-point input may be received from a camera on the glove and/or remote from the glove imaging the same portions of the glove making the same contact. Those two control-point inputs may be compared and used as the basis of calibration parameters when subsequent control-point inputs are received.

The detection of a touch-type contact or proximity sensor alert, which generate control-point input signals, may be used to calibrate image sensing of control-point activation conditions. Thus, when a conductive finger tip of a glove touches another conductive surface of the glove, the processor may be provided with a precise indication of where and when such contact was made. Accordingly, an image recognition system may then use images of the same event to determine calibration parameters that may be used to fine-tune/calibrate the image recognition system. The image recognition system may use machine learning/modeling to get a better idea of where one or more glove fingers actually are and how images look when those locations make contact with other predetermined surfaces on the glove or elsewhere. In addition, such calibration parameters may be used to subsequently identify the same finger or other portion of the glove merely hovering (i.e., not making contact), which may be associated with a different set of functions, operations, or a different virtual image of the relative position of the user's hand in a VR environment.

In determination block 1515, the processor may determine whether another control-point input has been received for simultaneously tracking location, angle, and/or relative position of the same one or more portions of the glove. Like the two control-point inputs used to determine the calibration parameters, another control-point input received following or coincident with the control-point input received in block 1410 may be used for updating or generating new calibration parameters. In response to the processor determining that another control-point input of this type has been received (i.e., determination block 1515="Yes"), the processor may compare the two control-point inputs to determine whether calibration parameters need to be saved or updated in block 1520.

In block 1530, the processor may save the calibration parameters or updated calibration parameters in response to determining the calibration parameters need to be saved or updated.

In response to the processor determining that no other control-point input of this type has been received (i.e., determination block 1515="No") or following the operations of block 1530, the processor may perform the operations of determination block 1415 of the method 1400 (FIG. 14).

A further aspect of various embodiments relates to virtual hand scaling. Various embodiments perform dynamic virtual hand scaling in order to present wearers of the gloves with a more realistic representation of their actual hand size. Glove size may not be an accurate representation of the size of the wearer's hands since the gloves may be made of elastic material that may shrink or stretch as much as 40%. In one aspect of dynamic virtual hand scaling, a processor may analyze images of the glove worn by the user, such as images received from wrist-mounted cameras (e.g., 970) or even images received from headset-mounted cameras, as shown in FIG. 10. In addition, the processor may compare the analyzed images to dimensions of an object of known size and position relative to the glove. Thus, a comparison of the analyzed images with known parameters may lead to a more accurate determination of glove size.

Figure 16:
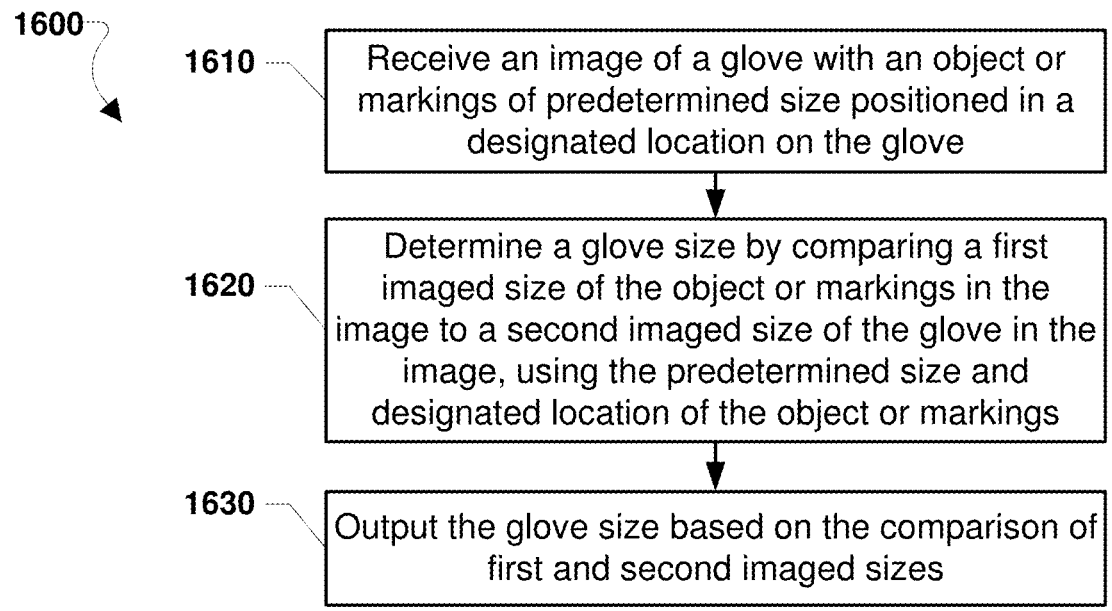
FIG. 16 is a process flow diagram of a method of virtual hand scaling according to various embodiments.

FIG. 16 illustrates an example method 1600 that may be implemented in a processor or computing device coupled to a glove 100 according to various embodiments. With reference to FIGS. 1-16, the method 1600 may be performed by a processor, such as a processor (e.g., 150) in the glove (e.g., 100, 200, 300, 305, 600, 700), a headset or headset camera (e.g., 1010) or another computing device (e.g., 1900 illustrated in FIG. 19). For ease of reference, the device executing operations of the method 1600 is referred to herein generally as a "processor."

In block 1610, the processor may receive an image of a glove with an object or markings of predetermined size positioned in a designated location on the glove. For example, an image of a logo or other graphic of known size and that may be found in the same location on numerous different gloves may be the object or markings used to perform dynamic virtual hand scaling. Similarly, a power pack, control module, or other object mounted in a designated location on the glove may also be used in this way.

In block 1620, the processor may determine a glove size by comparing a first imaged size of the object or markings in the image to a second imaged size of the glove in the image, using the predetermined size and designated location of the object or markings.

In block 1630, the processor may output the glove size based on the comparison of first and second imaged sizes.

A further aspect of various embodiments relates to virtual hand orienting. Various embodiments perform dynamic virtual hand orienting in order to present wearers of the gloves with a more accurate representation of virtual hand orientations. In one aspect of dynamic virtual hand orienting, a processor may analyze images of the glove worn by the user, such as images received from wrist-mounted cameras (e.g., 970) or even images received from headset-mounted cameras, as shown in FIG. 10. In addition, the processor may compare the analyzed images to dimensions of an object of known size and position relative to the glove. Further, the processor may also use data from other included sensors, such as inertial or magnetic sensors (e.g., 6 DOF or 9 DOF) to provide tilt-compensation and additional data for orientation. Thus, a comparison of the analyzed images with known parameters may lead to a more accurate determination of glove orientation.

Figure 17:
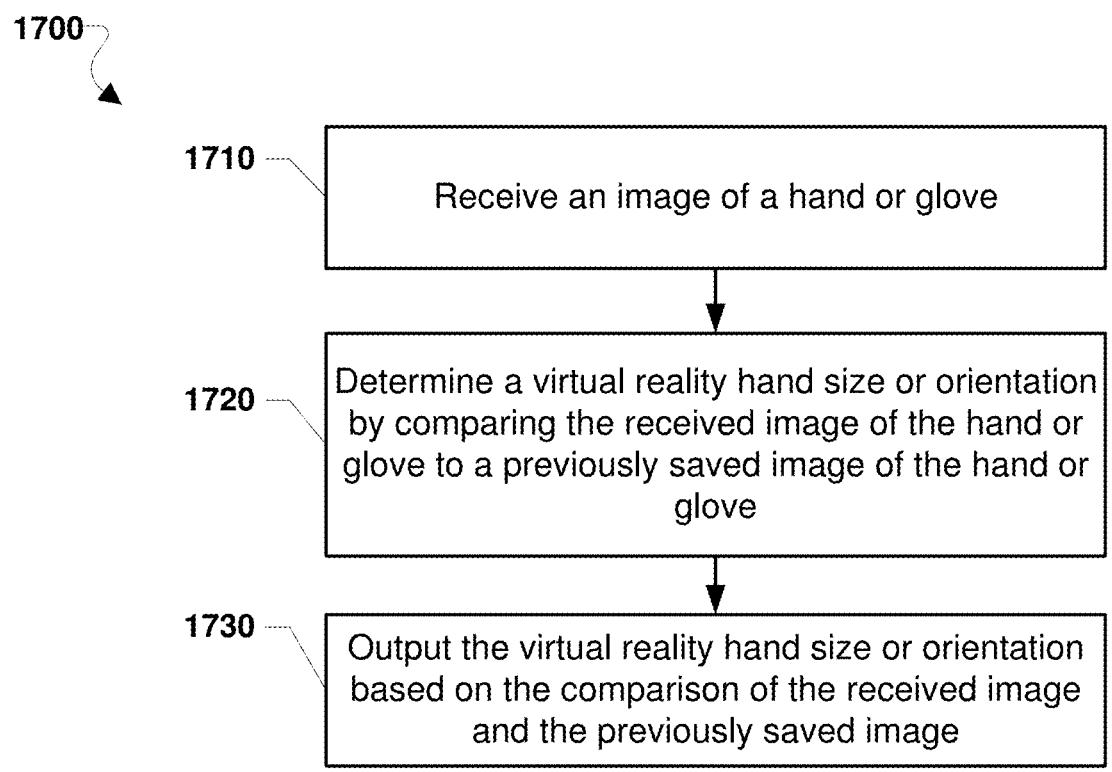
FIG. 17 is a process flow diagram of a method of virtual hand orienting according to various embodiments.

FIG. 17 illustrates an example method 1700 that may be implemented in a processor or computing device coupled to a glove (e.g., 100, 200, 300, 305, 600, 700) according to various embodiments. With reference to FIGS. 1-17, the method 1700 may be performed by a processor (e.g., 150) in the glove, a headset, headset camera (e.g., 70), or another computing device (e.g., 1900 illustrated in FIG. 19). For ease of reference, the device executing operations of the method 1700 is referred to herein generally as a "processor."

In block 1710, the processor may receive an image of a hand or glove with an object or markings of predetermined size positioned in a designated location on the glove. For example, an image of a logo or other graphic of known size and that may be found in the same location on numerous different gloves may be the object or markings used to perform dynamic virtual hand scaling. Similarly, a power pack, control module, or other object mounted in a designated location on the glove may also be used in this way.

In some embodiments, the received image of the hand or glove may include indications of a visible object or markings of predetermined size positioned in a designated location on the glove. Using the indications of the visible object or markings, the virtual reality hand size or orientation may be determined by comparing a first imaged size and orientation of the object or markings in the received image to the previously saved image of the glove.

In block 1720, the processor may determine a virtual reality hand size or orientation by comparing the received image of the hand or glove to a previously saved image of the hand or glove.

In block 1730, the processor may output the virtual reality hand size or orientation based on the comparison of the received image and the previously saved image.

A further aspect of various embodiments relates to control-point activation conditions detection. Various embodiments perform smart location cycling, which takes into account the most frequent locations and/or most recently active locations on the glove, in order to speed up the identification of where control-point activation conditions may be occurring.

Figure 18:
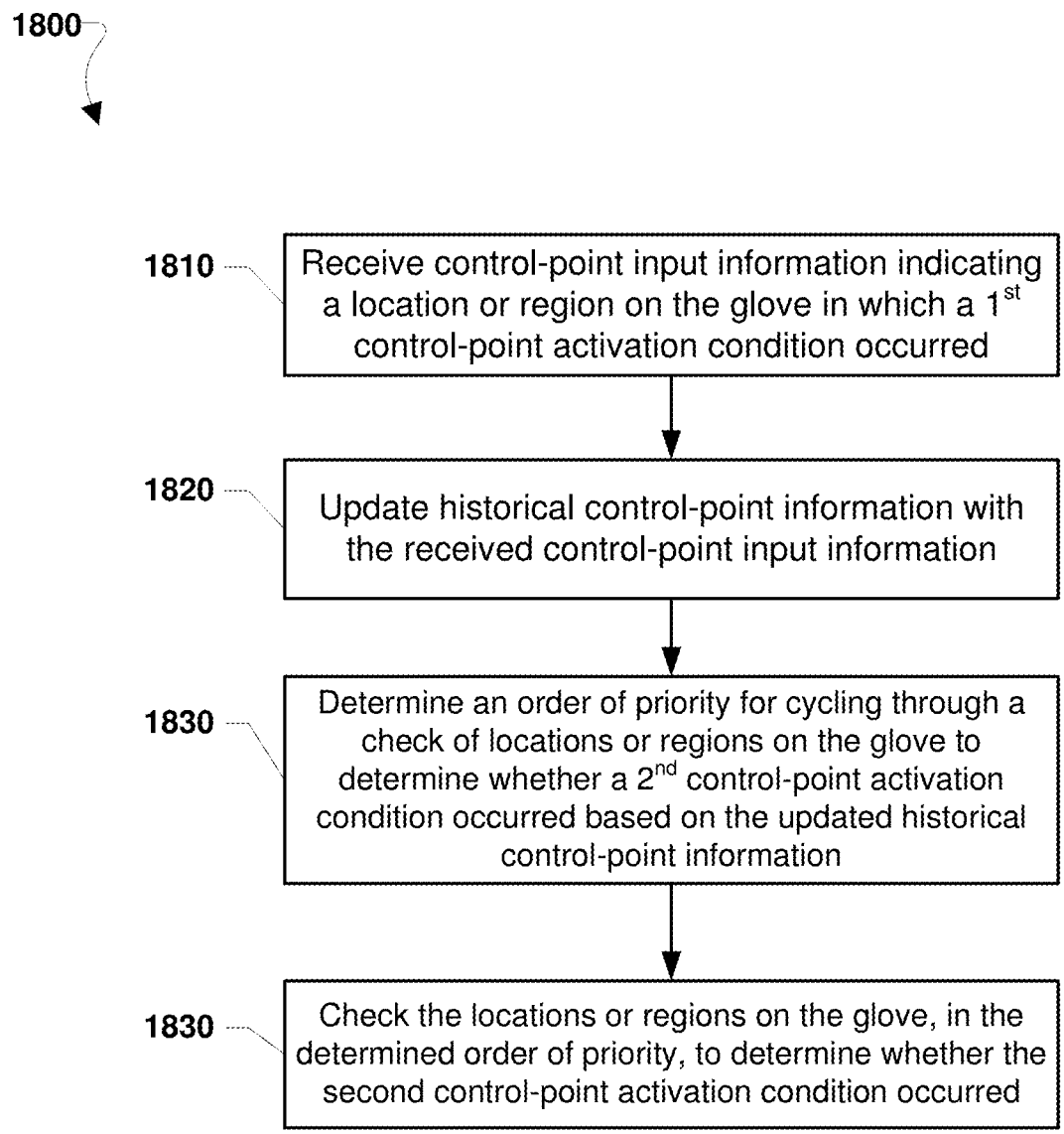
FIG. 18 is a process flow diagram of a method of determining an order of priority for cycling through a check of locations on the glove to determine whether control-point activation conditions are occurring according to various embodiments.

FIG. 18 illustrates an example method 1800 that may be implemented in a processor or computing device coupled to a glove 100 according to various embodiments. With reference to FIGS. 1-18, the method 1800 may be performed by a processor, such as a processor (e.g., 150) in the glove (e.g., 100, 200, 300, 305, 600, 700), a headset or headset camera (e.g., 70) or another computing device (e.g., 1900 illustrated in FIG. 19). For ease of reference, the device executing operations of the method 1800 is referred to herein generally as a "processor."

Various embodiments may include a method of prioritizing a search for locations or regions in which control-point activation conditions may exist. The prioritized search may determine an order and/or frequency with which to scan locations or regions using a search algorithm, known as a Baier algorithm or method. Using the Baier methods, the prioritized search may scan more frequently and/or more recently used locations or regions of a glove first and/or more often for control-point activation conditions, which may increase the speed in which control-point activation conditions may be detected. Some embodiments may modify the order of the prioritized search to account for common circumstances, customized settings/environments, or other situations if needed. In fact, the prioritized search may scan certain areas multiple times before scanning other areas.

For example, with reference to FIG. 1, consider a standard search and a prioritized search for locations or regions in which control-point activation conditions may exist. The standard search may cycle through looking for signals from the four expanded conductive areas 130a-130d, other than the thumb-tip conductive pad 130e. If each scan of each location takes 9 milliseconds (ms), two scans of the four expanded conductive areas 130a-130d will take 72 ms (i.e., 9×4×2=72). In contrast, a prioritized search may be executed much more quickly. For example, consider a prioritized search that focuses on looking for a pinching gesture (i.e., a pinch priority search) in which the pointer fingertip (i.e., at the expanded conductive area 130d) touches the thumb tip (thumb-tip conductive pad 130e). The pinch priority search may scan only the pointer fingertip and the thumb tip twice, to identify when a pinch gesture was made, much more quickly than scanning all the four finger tips.

In block 1810, the processor may receive control-point input information indicating a location or region on the glove in which a first control-point activation condition occurred. The location or region associated with the received control-point input information may be correlated to one of the expanded conductive areas (e.g., 130a-130e, 132a-132g, and 134a-134d) or a point along a conductive path (e.g., 120) on the glove.

In block 1820, the processor may update historical control-point information with the received control-point input information.

In block 1830, the processor may determine an order of priority for cycling through a check of locations or regions on the glove to determine whether a second control-point activation condition occurred based on the updated historical control-point information. In this way, the most frequently detected locations or regions (i.e., locations or regions on the glove in which control-point activation conditions are detected) may be given priority over less frequently detected or never detected locations or regions.

In block 1840, the processor may check the locations or regions on the glove, in the determined order of priority, to determine whether the second control-point activation condition occurred.

Alternatively, rather than making scanning priority adjustments based on the last control-point activation detection, the processor may use a standard scanning sequence, such as one determined to be the most efficient for the most common circumstances.

Figure 19:
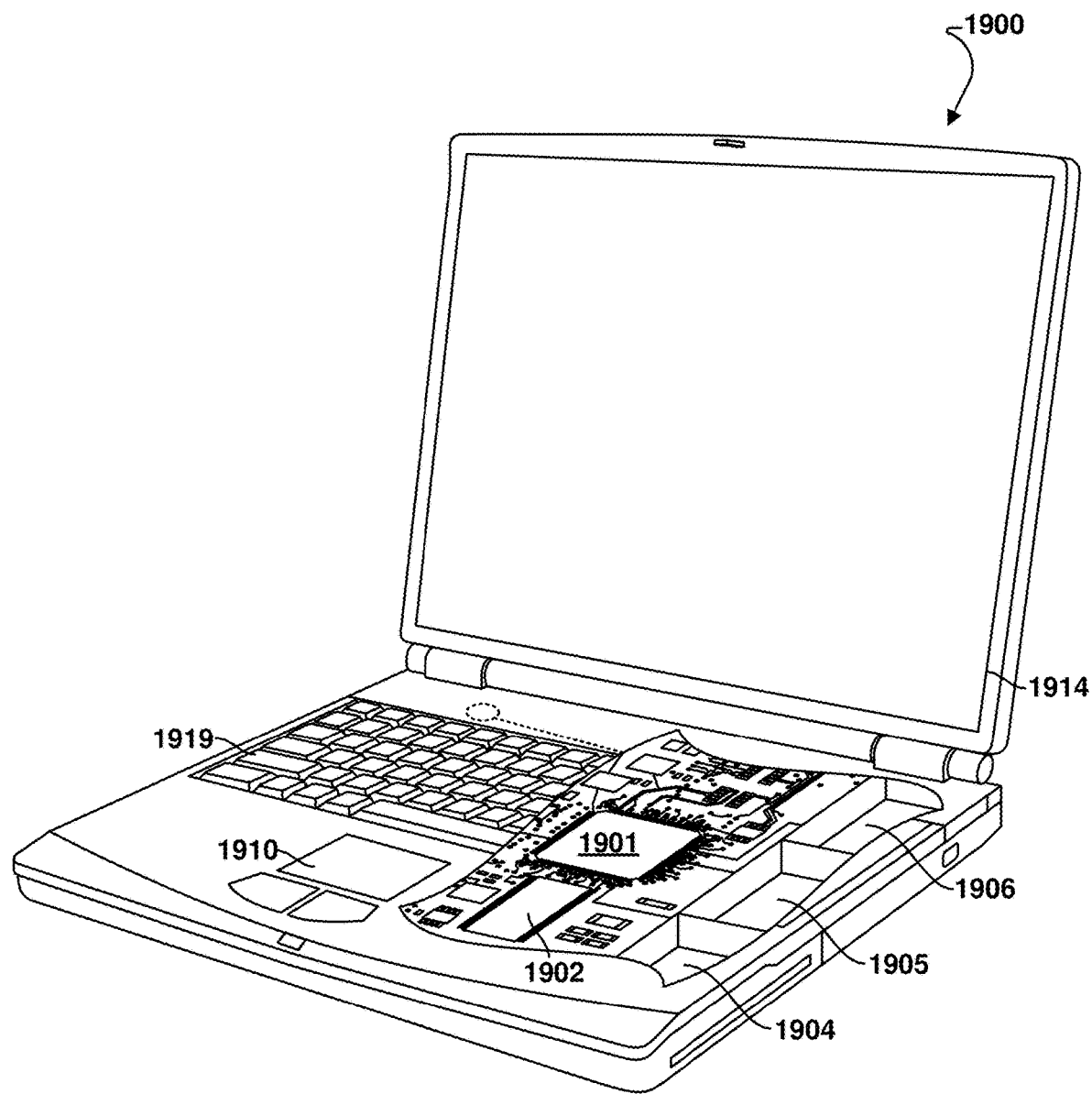
FIG. 19 is a block diagram of a computing device that may be configured to receive signals from one or more gloves according to various embodiments and implement a method according to various embodiments.

Various embodiment gloves may be connected to and various embodiment methods may be implemented in a variety of computing devices, such as a laptop computer 1900 as illustrated in FIG. 19. A laptop computer 1900 will typically include a processor 1901 coupled to volatile memory 1902, and a large capacity nonvolatile memory, such as a disk drive 1904 of Flash memory. The laptop computer 1900 may also include a floppy disc drive 1905 coupled to the processor 1906. The laptop computer 1900 may also include a number of connector ports or other network interfaces coupled to the processor 1901 for establishing data connections or receiving external memory receiver devices, such as a Universal Serial Bus (USB) or FireWire® connector sockets, or other network connection circuits for coupling the processor 1901 to a network (e.g., a communications network). In a notebook configuration, the computer housing includes the touchpad 1910, the keyboard 1912, and the display 1914 all coupled to the processor 1901. Other configurations of computing devices may include a computer mouse or trackball coupled to the processor (e.g., via a USB input) as are well known, which may also be used in conjunction with various embodiments.

The processors may be any programmable microprocessor, microcomputer or multiple processor chip or chips that may be configured by software instructions (applications) to perform a variety of functions, including the functions of the various embodiments described in this application. In some mobile devices, multiple processors may be provided, such as one processor dedicated to wireless communication functions and one processor dedicated to running other applications. Typically, software applications may be stored in the internal memory before they are accessed and loaded into the processor. The processor may include internal memory sufficient to store the application software instructions.

Various embodiments illustrated and described are provided merely as examples to illustrate various features of the claims. However, features shown and described with respect to any given embodiment are not necessarily limited to the associated embodiment and may be used or combined with other embodiments that are shown and described. Further, the claims are not intended to be limited by any one example embodiment. For example, one or more of the operations of the methods may be substituted for or combined with one or more operations of the methods.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the claims.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more embodiments, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

What is claimed is:

1. A method performed by a processor for control-point activation detection for generating control signals, the method comprising:

receiving a control-point input indicating a location or region on a glove in which a first control-point activation condition occurred, wherein the control-point activation condition corresponds to the location or region on a glove body of the glove coming in contact with or being within a threshold distance from at least one of another portion of the glove body or a control surface physically separate from the glove body;

updating historical control-point information with the received control-point input;

determining an order of priority for cycling through a check of locations or regions on the glove to determine whether a second control-point activation condition occurred based on the updated historical control-point information; and checking the location or region on the glove, in the determined order of priority, to determine whether the second control-point activation condition occurred.

2. The method of claim 1, wherein the order of priority for cycling through the check of locations or regions on the glove includes a highest priority for at least one most frequently detected location or region on the glove in which control-point activation conditions have been detected.

3. The method of claim 1, wherein the order of priority for cycling through the check of locations or regions on the glove includes a lowest priority for at least one least frequently detected location or region on the glove in which control-point activation conditions have been detected or a location or region on the glove in which control-point activation conditions have never been detected.

4. The method of claim 1, wherein the order of priority for cycling through the check of locations or regions on the glove includes a most efficient order of priority for the most common circumstances.

5. The method of claim 1, wherein the order of priority for cycling through the check of locations or regions on the glove includes locations or regions of the glove associated with the finger tips other than the thumb.

6. The method of claim 1, wherein the determined order of priority corresponds to a pinch priority search that focuses on looking for a pinching gesture in which the pointer finger touches the thumb tip.

7. The method of claim 1, wherein the determined order of priority considers as least one of common circumstances, customized settings, or customized environments.

8. The method of claim 1, wherein the determined order of priority scans at least one location or region on the glove multiple times before scanning at least one other location or region on the glove.

9. The method of claim 1, further comprising:
   adjusting a frequency with which to scan locations or regions on the glove.

\* \* \* \* \*